(12) United States Patent
Sheppard et al.

(10) Patent No.: US 6,395,890 B1
(45) Date of Patent: May 28, 2002

(54) NUCLEIC ACIDS ENCODING CONNECTIVE TISSUE GROWTH FACTOR HOMOLOGS

(75) Inventors: Paul O. Sheppard, Redmond; Stephen R. Jaspers, Edmonds; Zeren Gao, Redmond, all of WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 09/253,316

(22) Filed: Feb. 19, 1999

Related U.S. Application Data
(60) Provisional application No. 60/075,300, filed on Feb. 20, 1998.

(51) Int. Cl.[7] .............................................. C07H 21/04

(52) U.S. Cl. .................................. 536/23.5; 536/24.31

(58) Field of Search .............................. 536/23.5, 23.4, 536/24.31; 435/69.1, 69.4, 69.8, 325, 252.3, 320.1; 530/351, 399

(56) References Cited

U.S. PATENT DOCUMENTS

| | | | | |
|---|---|---|---|---|
| 5,194,596 A | * | 3/1993 | Tischer et al. .............. | 530/399 |
| 5,350,836 A | * | 9/1994 | Kopchick et al. ........... | 530/399 |
| 5,408,040 A | * | 4/1995 | Grotendorst et al. ........ | 530/399 |

FOREIGN PATENT DOCUMENTS

WO 99/21998 5/1999

OTHER PUBLICATIONS

A. Gladwin et al., Human Molecular Genetics 6(1):123–127, 1997.*
N. Braverman et al., Nature Genetics 15:369–376, 1997.*
C.C. Pilbeam et al., "Comparison of the effects of various lengths of synthetic human parathyroid hormone–related peptide (hPTHrP) of malignancy on bone resorption and formation in organ culture." Bone 14:717–720, 1993.*
S. Vukicevic et al., "Induction of nephrogenic mesenchyme by osteogenic protein 1 (bone morphogenic protein 7)", Proc. Nat. Acad. Sci. USA 93:9021–9026, 1996.*
J. Massague, "The TGF-β family of growth and differentiation factors." Cell 49:437–438, 1987.*
L. E. Benjamin et al., "Aj plasticity window for blood vessel remodeling is defined by pericyte coverage of the preformed endothelial network and is regulated by PDGF–B and VEGF." Development 125:1591–1598, 1998.*
J. Skolnick et al., "From genes to protein structure and function: novel applications of computational approaches in the genomic era", Trends in Biotech 18(1):34–39, 2000.*
P. Bork, "Powers and pitfalls in sequence analysis: The 70% hurdle", Genome Research 10:396–400, 2000.*
T. Doerks et al., "Protein annotation: detective work for function prediction", Trends in Genetics, 4(g):248–250, Jun. 1998.*

T.F. Smith et al., The challenge of genome sequence annotation or "The devil is in the details", Nature Biotechnology 15:1222–1223, 1997.*
S.E. Brenner, "Errors in genome annotation"Trends in Genetics 15(4) 132–133, 1999.*
P. Bork, "Go hunting in sequence databases but watch out for the traps", Trends in Genetics 12(10):425–426, 1996.*
R. Strausberg, Loci AW592899 and AA592984, 1997, National Cancer Institute Cancer Genome Anatomy Project, Tumor Gene Index, Accessed Aug. 21, 2000 (see attached computer printout).*
LIFESEQ™ Clone Information Results (INC555067), Incyte Pharmaceuticals, Inc., 1995.
LIFESEQ™ Clone Information Results (INC2509339), Incyte Pharmaceuticals, Inc., 1997.
LIFESEQ™ Clone Information Results (INC3208053), Incyte Pharmaceuticals, Inc., 1997.
LIFESEQ™ Clone Information Results (INC3941821), Incyte Pharmaceuticals, Inc., 1997.
LIFESEQ™ Clone Information Results (INC3036490), Incyte Pharmaceuticals, Inc., 1998.
Strausberg, Cancer Genome Anatomy Project, Genbank Acc. No. AA592984, 1997.
Strausberg, Cancer Genome Anatomy Project, Genbank Acc. No. AA897322, 1997.
Marra et al., WashU–HHMI Mouse EST Project, Genbank Acc. No. AA200958, 1996.
Marra et al., WashU–HHMI Mouse EST Project, Genbank Acc. No. AA764003, 1996.
Marra et al., WashU–HHMI Mouse EST Project, Genbank Acc. No. AA840452, 1996.
LIFESEQ™ Library Information Results (BRAUNT01), Incyte Pharmaceuticals, Inc., date unknown.
LIFESEQ™ Library Information Results (SCORNOT04), Incyte Pharmaceuticals, Inc., date unknown.
LIFESEQ™ Library Information Results (PENCNOT03), Incyte Pharmaceuticals, Inc., date unknown.
LIFESEQ™ Library Information Results (SCORNOT01), Incyte Pharmaceuticals, Inc., date unknown.
LIFESEQ™Library Information Results (CONUTUT01), Incyte Pharmaceuticals, Inc., date unknown.
Tubby, Acc. No. Z99289, 1997.
Hurvitz, et al., Nature Genetics 23: 94–98, 1999.
Pennica et al., Proc. Natl. Acad. Sci. U.S.A. 95: 14717–14722, 1998.

\* cited by examiner

Primary Examiner—Lorraine Spector
(74) Attorney, Agent, or Firm—Deborah A. Sawislak

(57) ABSTRACT

This present invention is directed to polypeptide and polynucleotide molecules that encode a new connective tissue growth factor homolog polypeptide. The human polypeptides have been designated zCTGF4 and the mouse orthologs have been designated zCTGF2. The invention also includes antibodies, expression vectors, host cells expressing zCTGF4 and variants. Also included are methods for producing the polypeptides and using the polynucleotides and polypeptides.

1 Claim, 2 Drawing Sheets

```
                10        20        30        40        50
NOV_HU   MQSVQSTSFCLRKQCLCLTFLLLHLLGQVAAT-----------------  32
CTGF_H   MTAASMGPVRVAFVVLLALCSRPAVG-----------------------  26
zctgf2M  -------------------------------------------------   0
zctgf4H  MQGLLFPTLLLAGLAQFCCRVQG---------------TGPLDTTPEGRP  35
IBP1_H   MSEVPVARVWLVLLLLTVQVGVTAG------------------------  25
IBP2_H   MLPRVGCPALPLPPPPLLPLLLLLLGASG-GGGGARAEVLFRCPPCT   49

60        70        80        90       100
NOV_HU   ----------QRCPPQCPGRCPATP-PTCAPGVRAVLDGCSCCLVCARQR  71
CTGF_H   ----------QNCSGPCR--CPDEPAPRCPAGVSLVLDGCGCCRVCAKQL  64
zctgf2M  -------------------------------------------------   0
zctgf4H  GEVSDAPQRKQFCHWPCK--CPQQK-PRCPPGVSLVRDGCGCCKICAKQP  82
IBP1_H   ---APWQCAPCSAEKLAL--CPPVS-ASCSEVTR--SAGCGCCPMCALPL  67
IBP2_H   PERLAACGPPPVAPPAAVAAVAGGARMPCAELVR--EPGCGCCSVCARLE  97

110       120       130       140       150
NOV_HU   GESCSDLEPCDESSGLYCDRSADPSN-QTGICTAVEGD-NCVFDGVIYRS 119
CTGF_H   GELCTERDPCDPHKGLFCDFGSPANR-KIGVCTAKDGA-PCIFGGTVYRS 112
zctgf2M  -------------------------------------------------   0
zctgf4H  GEICNEADLCDPHKGLYCDYSVDRPRYETGVCAYLVAV-GCEFNQVHYHN 131
IBP1_H   GAACGVATARCARGLSCR-------------------------------  85
IBP2_H   GEACGVYTPRCGQGLRCY------------------------------- 115

160       170       180       190       200
NOV_HU   GEKFQPSCKFQCTCRDGQIGCVPRCQLDVLLPEPNCPAPRKVEVPGECCE 169
CTGF_H   GESFQSSCKYQCTCLDGAVGCMPLCSMDVRLPSPDCPFPRRVKLPGKCCE 162
zctgf2M  -------------------------------------------------   0
zctgf4H  GQVFQPNPLFSCLCVSGAIGCTPL--FIPKLAGSHCSGAK----GGKKSD 175
IBP1_H   -------------------------------------------------  85
IBP2_H   ------------------------------------------------- 115

210       220       230       240       250
NOV_HU   KWICGPDEEDSLGGL---TLAAYRPEATLGVEVSDSSVNCIEQTTEWTAC 216
CTGF_H   EWVC--DEPK-DQTVVGPALAAYRLEDTFGPDPTMIRANCLVQTTEWSAC 209
zctgf2M  -------------------NVVYLPAYRNLPLIWKKKCLVQATKWTPC   29
zctgf4H  QSNC--SLEP----LLQQLSTSYKTMPAYRNLPLIWKKKCLVQATKWTPC 219
IBP1_H   -------------------------------------------------  85
IBP2_H   ------------------------------------------------- 115
```

Fig. 1A

```
           260        270        280        290        300
NOV_HU   SKSCGMGFSTRVTNRNRQCEMLKQTRLCMVRPCEQEPEQ-PTDKKGKKCL  265
CTGF_H   SKTCGMGISTRVTNDNASCRLEKQSRLCMVRPCEADLE--ENIKKGKKCI  257
ZCTGF2M  S---------------------------------------IPRGETCQ    38
zctgf4H  SRTCGMGISNRVTNENSNCEMRKEKRLCYIQPCDSNILKTIKIPKGKTCQ  269
IBP1_H   --------------------------------------------------  85
IBP2_H   --------------------------------------------------  115

310        320        330        340        350
NOV_HU   RT-KKSLKAIHLQFKNCTSLHTYKPRFCGVCSDGRCCTPHNTKTIQAEFQ  314
CTGF_H   RTPKISKPIKFE-LSGCTSMKTYRAKFCGVCTDGRCCTPHRTTTLPVEFK  306
ZCTGF2M  PTFQLPKAEKFV-FSGCSSTQSYRPTFCGICLDKRCCVPNKSKMITVRFD   87
zctgf4H  PTFQLSKAEKFV-FSGCSSTQSYKPTFCGICLDKRCCIPNKSKMITIQFD  318
IBP1_H   --------------------------------------------------  85
IBP2_H   --------------------------------------------------  115

360        370        380        390
NOV_HU   CSPGQIVKKPVMVIGTCTCHTNCPKNNEAFLQELELKTTRGK--  356
CTGF_H   CPDGEVMKKNMMFIKTCACHYNCPGDNDIFESLYYRKMYGDM--  348
ZCTGF2M  CPSEGSFKWQMLWVTSCVCQRDCREPGDIFSELRIL--------  123
zctgf4H  CPNEGSFKWKMLWITSCVCQRNCREPGDIFSELKIL--------  354
IBP1_H   -------------------------------------------   85
IBP2_H   -------------------------------------------  115
```

Fig. 1B

SEQUENCE LISTING

<160> NUMBER OF SEQ ID NOS: 34

<210> SEQ ID NO 1
<211> LENGTH: 1142
<212> TYPE: DNA
<213> ORGANISM: Homo sapiens
<220> FEATURE:
<221> NAME/KEY: CDS
<222> LOCATION: (17)...(1078)

<400> SEQUENCE: 1

```
ccacggtccc agcgac atg cag ggg ctc ctc ttc ccc act ctt ctg ctt gct      52
                Met Gln Gly Leu Leu Phe Pro Thr Leu Leu L eu Ala
                 1               5                  10 ggc ctg gca cag ttc tgc tgc agg gta cag g gc act gga cca tta gat     100
Gly Leu Ala Gln Phe Cys Cys Arg Val Gln G ly Thr Gly Pro Leu Asp
         15                  20                  25
```

-continued

```
aca aca cct gaa gga agg cct gga gaa gtg t ca gat gca cct cag cgt         148
Thr Thr Pro Glu Gly Arg Pro Gly Glu Val S er Asp Ala Pro Gln Arg
     30                  35                  40 aaa cag ttt tgt cac tgg ccc tgc aaa tgc c ct cag cag aag ccc cgt         196
Lys Gln Phe Cys His Trp Pro Cys Lys Cys P ro Gln Gln Lys Pro Arg
 45                  50                  55                  60 tgc cct cct gga gtg agc ctg gtg aga gat g gc tgt gga tgc tgt aaa         244
Cys Pro Pro Gly Val Ser Leu Val Arg Asp G ly Cys Gly Cys Cys Lys
                 65                  70                  75 atc tgt gcc aag caa cca ggg gaa atc tgc a at gaa gct gac ctc tgt         292
Ile Cys Ala Lys Gln Pro Gly Glu Ile Cys A sn Glu Ala Asp Leu Cys
             80                  85                  90 gac cca cac aaa ggg ctg tat tgt gac tac t ca gta gac agg cct agg         340
Asp Pro His Lys Gly Leu Tyr Cys Asp Tyr S er Val Asp Arg Pro Arg
         95                  100                 105 tac gag act gga gtg tgt gca tac ctt gta g ct gtt ggg tgc gag ttc         388
Tyr Glu Thr Gly Val Cys Ala Tyr Leu Val A la Val Gly Cys Glu Phe
     110                 115                 120 aac cag gta cat tat cat aat ggc caa gtg t tt cag ccc aac ccc ttg         436
Asn Gln Val His Tyr His Asn Gly Gln Val P he Gln Pro Asn Pro Leu
125                 130                 135                 140 ttc agc tgc ctc tgt gtg agt ggg gcc att g ga tgc aca cct ctg ttc         484
Phe Ser Cys Leu Cys Val Ser Gly Ala Ile G ly Cys Thr Pro Leu Phe
                 145                 150                 155 ata cca aag ctg gct ggc agt cac tgc tct g ga gct aaa ggt gga aag         532
Ile Pro Lys Leu Ala Gly Ser His Cys Ser G ly Ala Lys Gly Gly Lys
             160                 165                 170 aag tct gat cag tca aac tgt agc ctg gaa c ca tta cta cag cag ctt         580
Lys Ser Asp Gln Ser Asn Cys Ser Leu Glu P ro Leu Leu Gln Gln Leu
         175                 180                 185 tca aca agc tac aaa aca atg cca gct tat a ga aat ctc cca ctt att         628
Ser Thr Ser Tyr Lys Thr Met Pro Ala Tyr A rg Asn Leu Pro Leu Ile
     190                 195                 200 tgg aaa aaa aaa tgt ctt gtg caa gca aca a aa tgg act ccc tgc tcc         676
Trp Lys Lys Lys Cys Leu Val Gln Ala Thr L ys Trp Thr Pro Cys Ser
205                 210                 215                 220 aga aca tgt ggg atg gga ata tct aac agg g tg acc aat gaa aac agc         724
Arg Thr Cys Gly Met Gly Ile Ser Asn Arg V al Thr Asn Glu Asn Ser
                 225                 230                 235 aac tgt gaa atg aga aaa gag aaa aga ctg t gt tac att cag cct tgc         772
Asn Cys Glu Met Arg Lys Glu Lys Arg Leu C ys Tyr Ile Gln Pro Cys
             240                 245                 250 gac agc aat ata tta aag aca ata aag att c cc aaa gga aaa aca tgc         820
Asp Ser Asn Ile Leu Lys Thr Ile Lys Ile P ro Lys Gly Lys Thr Cys
         255                 260                 265 caa cct act ttc caa ctc tcc aaa gct gaa a aa ttt gtc ttt tct gga         868
Gln Pro Thr Phe Gln Leu Ser Lys Ala Glu L ys Phe Val Phe Ser Gly
     270                 275                 280 tgc tca agt act cag agt tac aaa ccc act t tt tgt gga ata tgc ttg         916
Cys Ser Ser Thr Gln Ser Tyr Lys Pro Thr P he Cys Gly Ile Cys Leu
285                 290                 295                 300 gat aag aga tgc tgt atc cct aat aag tct a aa atg att act att caa         964
Asp Lys Arg Cys Cys Ile Pro Asn Lys Ser L ys Met Ile Thr Ile Gln
                 305                 310                 315 ttt gat tgc cca aat gag ggg tca ttt aaa t gg aag atg ctg tgg att        1012
Phe Asp Cys Pro Asn Glu Gly Ser Phe Lys T rp Lys Met Leu Trp Ile
             320                 325                 330 aca tct tgt gtg tgt cag aga aac tgc aga g aa cct gga gat ata ttt        1060
Thr Ser Cys Val Cys Gln Arg Asn Cys Arg G lu Pro Gly Asp Ile Phe
         335                 340                 345
```

```
tct gag ctc aag att ctg taaaaccaag caaatggggg a aaagttagt              1108
Ser Glu Leu Lys Ile Leu
        350 caatcctgtc atataataaa aaaattagtg agta                                   1142

<210> SEQ ID NO 2
<211> LENGTH: 354
<212> TYPE: PRT
<213> ORGANISM: Homo sapiens

<400> SEQUENCE: 2

Met Gln Gly Leu Leu Phe Pro Thr Leu Leu L eu Ala Gly Leu Ala Gln
  1               5                  10                  15

Phe Cys Cys Arg Val Gln Gly Thr Gly Pro L eu Asp Thr Thr Pro Glu
                 20                  25                  30

Gly Arg Pro Gly Glu Val Ser Asp Ala Pro G ln Arg Lys Gln Phe Cys
             35                  40                  45

His Trp Pro Cys Lys Cys Pro Gln Gln Lys P ro Arg Cys Pro Pro Gly
         50                  55                  60

Val Ser Leu Val Arg Asp Gly Cys Gly Cys C ys Lys Ile Cys Ala Lys
 65                  70                  75                   80

Gln Pro Gly Glu Ile Cys Asn Glu Ala Asp L eu Cys Asp Pro His Lys
                 85                  90                  95

Gly Leu Tyr Cys Asp Tyr Ser Val Asp Arg P ro Arg Tyr Glu Thr Gly
            100                 105                 110

Val Cys Ala Tyr Leu Val Ala Val Gly Cys G lu Phe Asn Gln Val His
            115                 120                 125

Tyr His Asn Gly Gln Val Phe Gln Pro Asn P ro Leu Phe Ser Cys Leu
130                 135                 140

Cys Val Ser Gly Ala Ile Gly Cys Thr Pro L eu Phe Ile Pro Lys Leu
145                 150                 155                 160

Ala Gly Ser His Cys Ser Gly Ala Lys Gly G ly Lys Lys Ser Asp Gln
                165                 170                 175

Ser Asn Cys Ser Leu Glu Pro Leu Leu Gln G ln Leu Ser Thr Ser Tyr
            180                 185                 190

Lys Thr Met Pro Ala Tyr Arg Asn Leu Pro L eu Ile Trp Lys Lys Lys
            195                 200                 205

Cys Leu Val Gln Ala Thr Lys Trp Thr Pro C ys Ser Arg Thr Cys Gly
    210                 215                 220

Met Gly Ile Ser Asn Arg Val Thr Asn Glu A sn Ser Asn Cys Glu Met
225                 230                 235                 240

Arg Lys Glu Lys Arg Leu Cys Tyr Ile Gln P ro Cys Asp Ser Asn Ile
                245                 250                 255

Leu Lys Thr Ile Lys Ile Pro Lys Gly Lys T hr Cys Gln Pro Thr Phe
            260                 265                 270

Gln Leu Ser Lys Ala Glu Lys Phe Val Phe S er Gly Cys Ser Ser Thr
            275                 280                 285

Gln Ser Tyr Lys Pro Thr Phe Cys Gly Ile C ys Leu Asp Lys Arg Cys
    290                 295                 300

Cys Ile Pro Asn Lys Ser Lys Met Ile Thr I le Gln Phe Asp Cys Pro
305                 310                 315                 320

Asn Glu Gly Ser Phe Lys Trp Lys Met Leu T rp Ile Thr Ser Cys Val
                325                 330                 335

Cys Gln Arg Asn Cys Arg Glu Pro Gly Asp I le Phe Ser Glu Leu Lys
```

Ile Leu

<210> SEQ ID NO 3
<211> LENGTH: 1062
<212> TYPE: DNA
<213> ORGANISM: Artificial Sequence
<220> FEATURE:
<223> OTHER INFORMATION: Degenerate sequence
<220> FEATURE:
<221> NAME/KEY: misc_feature
<222> LOCATION: (1)...(1062)
<223> OTHER INFORMATION: n = A,T,C or G

<400> SEQUENCE: 3

| | | | | |
|---|---|---|---|---|
| atgcarggny | tnytnttycc | nacnytnytn | ytngcnggny | tngcncartt y tgytgymgn | 60 |
| gtncarggna | cnggnccnyt | ngayacnacn | ccngarggnm | gnccnggnga r gtnwsngay | 120 |
| gcnccncarm | gnaarcartt | ytgycaytgg | ccntgyaart | gyccncarca r aarccnmgn | 180 |
| tgyccnccng | gngtnwsnyt | ngtnmgngay | ggntgyggnt | gytgyaarat h tgygcnaar | 240 |
| carccnggng | arathtgyaa | ygargcngay | ytntgygayc | cncayaaggg n ytntaytgy | 300 |
| gaytaywsng | tngaymgncc | nmgntaygar | acnggngtnt | gygcntayyt n gtngcngtn | 360 |
| ggntgygart | tyaaycargt | ncaytaycay | aayggncarg | tnttycarcc n aayccnytn | 420 |
| ttywsntgyy | tntgygtnws | nggngcnath | ggntgyacnc | cnytnttyat h ccnaarytn | 480 |
| gcnggnwsnc | aytgywsngg | ngcnaarggn | ggnaaraarw | sngaycarws n aaytgywsn | 540 |
| ytngarccny | tnytncarca | rytnwsnacn | wsntayaara | cnatgccngc n taymgnaay | 600 |
| ytnccnytna | thtggaaraa | raartgyytn | gtncargcna | cnaartggac n ccntgywsn | 660 |
| mgnacntgyg | gnatgggnat | hwsnaaymgn | gtnacnaayg | araaywsnaa y tgygaratg | 720 |
| mgnaargara | armgnytntg | ytayathcar | ccntgygayw | snaayathyt n aaracnath | 780 |
| aarathccna | argnaarac | ntgycarccn | acnttycary | tnwsnaargc n garaartty | 840 |
| gtnttywsng | gntgywsnws | nacncarwsn | tayaarccna | cnttytgygg n athtgyytn | 900 |
| gayaarmgnt | gytgyathcc | naayaarwsn | aaratgatha | cnathcartt y gaytgyccn | 960 |
| aaygarggnw | snttyaartg | gaaratgytn | tggathacnw | sntgygtntg y carmgnaay | 1020 |
| tgymgngarc | cnggngayat | httywsngar | ytnaarathy tn | 1062 |

<210> SEQ ID NO 4
<211> LENGTH: 279
<212> TYPE: DNA
<213> ORGANISM: Mus musculus

<400> SEQUENCE: 4

| | | | | |
|---|---|---|---|---|
| atccccagag | gagaaacatg | tcaacccact | ttccaactcc | ccaaagctga a aaatttgtt | 60 |
| ttttctggat | gctcaagcac | tcagagttac | agacccactt | tctgtggaat a tgcctggac | 120 |
| aagagatgct | gtgtccccaa | caaatctaaa | atgattactg | ttaggtttga c tgccccagt | 180 |
| gaagggtcat | ttaagtggca | gatgctgtgg | gtcacatctt | gtgtgtgtca g agggactgc | 240 |
| agagaaccag | gagatatatt | ttctgagctc | aggattcta | | 279 |

<210> SEQ ID NO 5
<211> LENGTH: 93
<212> TYPE: PRT
<213> ORGANISM: Mus musculus

<400> SEQUENCE: 5

```
Ile Pro Arg Gly Glu Thr Cys Gln Pro Thr Phe Gln Leu Pro Lys Ala
 1               5                  10                  15

Glu Lys Phe Val Phe Ser Gly Cys Ser Ser Thr Gln Ser Tyr Arg Pro
                20                  25                  30

Thr Phe Cys Gly Ile Cys Leu Asp Lys Arg Cys Cys Val Pro Asn Lys
            35                  40                  45

Ser Lys Met Ile Thr Val Arg Phe Asp Cys Pro Ser Glu Gly Ser Phe
        50                  55                  60

Lys Trp Gln Met Leu Trp Val Thr Ser Cys Val Cys Gln Arg Asp Cys
 65                 70                  75                  80

Arg Glu Pro Gly Asp Ile Phe Ser Glu Leu Arg Ile Leu
                85                  90
```

<210> SEQ ID NO 6
<211> LENGTH: 22
<212> TYPE: DNA
<213> ORGANISM: Artificial Sequence
<220> FEATURE:
<223> OTHER INFORMATION: oligonucleotide primer ZC 14882

<400> SEQUENCE: 6
aactttcccc ccatttgctt gg                                           22

<210> SEQ ID NO 7
<211> LENGTH: 21
<212> TYPE: DNA
<213> ORGANISM: Artificial Sequence
<220> FEATURE:
<223> OTHER INFORMATION: oligonucleotide primer ZC 14883

<400> SEQUENCE: 7
acaaaatgga ctccctgctc c                                            21

<210> SEQ ID NO 8
<211> LENGTH: 22
<212> TYPE: DNA
<213> ORGANISM: Artificial Sequence
<220> FEATURE:
<223> OTHER INFORMATION: oligonucleotide primer ZC 15909

<400> SEQUENCE: 8
tcgtccaacg actataaaga gg                                           22

<210> SEQ ID NO 9
<211> LENGTH: 21
<212> TYPE: DNA
<213> ORGANISM: Artificial Sequence
<220> FEATURE:
<223> OTHER INFORMATION: oligonucleotide primer ZC 14885

<400> SEQUENCE: 9
ttgctgtcgc aaggctgaat g                                            21

<210> SEQ ID NO 10
<211> LENGTH: 21
<212> TYPE: DNA
<213> ORGANISM: Artificial Sequence
<220> FEATURE:
<223> OTHER INFORMATION: oligonucleotide primer ZC 15911

<400> SEQUENCE: 10
aggctgtcct ctaagcgtca c                                            21

```
<210> SEQ ID NO 11
<211> LENGTH: 21
<212> TYPE: DNA
<213> ORGANISM: Artificial Sequence
<220> FEATURE:
<223> OTHER INFORMATION: oligonucleotide primer ZC 14884

<400> SEQUENCE: 11
cacagttgct gttttcattg g                                              21

<210> SEQ ID NO 12
<211> LENGTH: 21
<212> TYPE: DNA
<213> ORGANISM: Artificial Sequence
<220> FEATURE:
<223> OTHER INFORMATION: oligonucleotide primer ZC 15910

<400> SEQUENCE: 12
ctgttgggtg cgagttcaac c                                              21

<210> SEQ ID NO 13
<211> LENGTH: 22
<212> TYPE: DNA
<213> ORGANISM: Artificial Sequence
<220> FEATURE:
<223> OTHER INFORMATION: oligonucleotide primer ZC 16192

<400> SEQUENCE: 13
tcataatggc caagtgtttc ag                                             22

<210> SEQ ID NO 14
<211> LENGTH: 18
<212> TYPE: DNA
<213> ORGANISM: Artificial Sequence
<220> FEATURE:
<223> OTHER INFORMATION: oligonucleotide primer ZC 15089

<400> SEQUENCE: 14
tccctaataa gtctaaaa                                                  18

<210> SEQ ID NO 15
<211> LENGTH: 18
<212> TYPE: DNA
<213> ORGANISM: Artificial Sequence
<220> FEATURE:
<223> OTHER INFORMATION: oligonucleotide primer ZC 15092

<400> SEQUENCE: 15
taacttttcc cccatttg                                                  18

<210> SEQ ID NO 16
<211> LENGTH: 6
<212> TYPE: PRT
<213> ORGANISM: Artificial Sequence
<220> FEATURE:
<223> OTHER INFORMATION: Peptide tag

<400> SEQUENCE: 16

Glu Tyr Met Pro Met Glu
 1               5

<210> SEQ ID NO 17
<211> LENGTH: 33
<212> TYPE: DNA
<213> ORGANISM: Artificial Sequence
<220> FEATURE:
```

```
<223> OTHER INFORMATION: oligonucleotide primer ZC 16422

<400> SEQUENCE: 17
tctataagct ggcattgttt tgtagcttgt tga                              33

<210> SEQ ID NO 18
<211> LENGTH: 30
<212> TYPE: DNA
<213> ORGANISM: Artificial Sequence
<220> FEATURE:
<223> OTHER INFORMATION: oligonucleotide primer ZC 16424

<400> SEQUENCE: 18
ccgggatcca ctggaccatt agatacaaca                                  30

<210> SEQ ID NO 19
<211> LENGTH: 33
<212> TYPE: DNA
<213> ORGANISM: Artificial Sequence
<220> FEATURE:
<223> OTHER INFORMATION: oligonucleotide primer ZC 16421

<400> SEQUENCE: 19
tacaaaacaa tgccagctta tagaaatctc cca                              33

<210> SEQ ID NO 20
<211> LENGTH: 30
<212> TYPE: DNA
<213> ORGANISM: Artificial Sequence
<220> FEATURE:
<223> OTHER INFORMATION: oligonucleotide primer ZC 16425

<400> SEQUENCE: 20
accctcgagt tacagaatct tgagctcaga                                  30

<210> SEQ ID NO 21
<211> LENGTH: 30
<212> TYPE: DNA
<213> ORGANISM: Artificial Sequence
<220> FEATURE:
<223> OTHER INFORMATION: oligonucleotide primer ZC 16423

<400> SEQUENCE: 21
accctcgaga tgcaggggct cctcttcccc                                  30

<210> SEQ ID NO 22
<211> LENGTH: 30
<212> TYPE: DNA
<213> ORGANISM: Artificial Sequence
<220> FEATURE:
<223> OTHER INFORMATION: oligonucleotide primer ZC 16409

<400> SEQUENCE: 22
ccgggatccc agaatcttga gctcagaaaa                                  30

<210> SEQ ID NO 23
<211> LENGTH: 127
<212> TYPE: PRT
<213> ORGANISM: Artificial Sequence
<220> FEATURE:
<223> OTHER INFORMATION: connective tissue growth factor family motif
<220> FEATURE:
<221> NAME/KEY: VARIANT
<222> LOCATION: (2)...(9)
<223> OTHER INFORMATION: Xaa is any amino ac id
<220> FEATURE:
<221> NAME/KEY: VARIANT
```

```
<222> LOCATION: (10)...(11)
<223> OTHER INFORMATION: Xaa is any amino ac id or not present
<220> FEATURE:
<221> NAME/K

```
<211> LENGTH: 40
<212> TYPE: PRT
<213> ORGANISM: Artificial Sequence
<220> FEATURE:
<223> OTHER INFORMATION: connective tissue growth factor family motif
<220> FEATURE:
<221> NAME/KEY: VARIANT
<222> LOCATION: (2)...(9)
<223> OTHER INFORMATION: Xaa is any amino ac id
<220> FEATURE:
<221> NAME/KEY: VARIANT
<222> LOCATION: (10)...(11)
<223> OTHER INFORMATION: Xaa is any amino ac id or not present
<220> FEATURE:
<221> NAME/KEY: VARIANT
<222> LOCATION: (13)...(13)
<223> OTHER INFORMATION: Xaa is any amino ac id
<220> FEATURE:
<221> NAME/KEY: VARIANT
<222> LOCATION: (16)...(17)
<223> OTHER INFORMATION: Xaa is any amino ac id
<220> FEATURE:
<221> NAME/KEY: VARIANT
<222> LOCATION: (19)...(25)
<223> OTHER INFORMATION: Xaa is any amino ac id
<220> FEATURE:
<221> NAME/KEY: VARIANT
<222> LOCATION: (27)...(31)
<223> OTHER INFORMATION: Xaa is any amino ac id
<220> FEATURE:
<221> NAME/KEY: VARIANT
<222> LOCATION: (32)...(32)
<223> OTHER INFORMATION: Xaa is any amino ac id or not present
<220> FEATURE:
<221> NAME/KEY: VARIANT
<222> LOCATION: (34)...(38)
<223> OTHER INFORMATION: Xaa is any amino ac id
<220> FEATURE:
<221> NAME/KEY: VARIANT
<222> LOCATION: (39)...(40)
<223> OTHER INFORMATION: Xaa is any amino ac id or not present

<400> SEQUENCE: 24

Cys Xaa Xaa Xaa Xaa Xaa Xaa Xaa Xaa X aa Cys Xaa Cys Cys Xaa
 1               5                  10                  15

Xaa Cys Xaa Xaa Xaa Xaa Xaa Xaa Cys X aa Xaa Xaa Xaa Xaa Xaa
            20                  25                  30

Cys Xaa Xaa Xaa Xaa Xaa Xaa Xaa
         35                  40

<210> SEQ ID NO 25
<211> LENGTH: 357
<212> TYPE: PRT
<213> ORGANISM: Homo sapiens

<400> SEQUENCE: 25

Met Gln Ser Val Gln Ser Thr Ser Phe Cys L eu Arg Lys Gln Cys Leu
 1               5                  10                  15

Cys Leu Thr Phe Leu Leu Leu His Leu G ly Gln Val Ala Ala Thr
            20                  25                  30

Gln Arg Cys Pro Pro Gln Cys Pro Gly Arg C ys Pro Ala Thr Pro Pro
         35                  40                  45

Thr Cys Ala Pro Gly Val Arg Ala Val Leu A sp Gly Cys Ser Cys Cys
     50                  55                  60

Leu Val Cys Ala Arg Gln Arg Gly Glu Ser C ys Ser Asp Leu Glu Pro
65                  70                  75                  80

Cys Asp Glu Ser Ser Gly Leu Tyr Cys Asp A rg Ser Ala Asp Pro Ser
                 85                  90                  95
```

```
Asn Gln Thr Gly Ile Cys Thr Ala Val Glu Gly Asp Asn Cys Val Phe
                100                 105                 110

Asp Gly Val Ile Tyr Arg Ser Gly Glu Lys Phe Gln Pro Ser Cys Lys
            115                 120                 125

Phe Gln Cys Thr Cys Arg Asp Gly Gln Ile Gly Cys Val Pro Arg Cys
130                 135                 140

Gln Leu Asp Val Leu Pro Glu Pro Asn Cys Pro Ala Pro Arg Lys
145                 150                 155                 160

Val Glu Val Pro Gly Glu Cys Cys Glu Lys Trp Ile Cys Gly Pro Asp
                165                 170                 175

Glu Glu Asp Ser Leu Gly Gly Leu Thr Leu Ala Ala Tyr Arg Pro Glu
            180                 185                 190

Ala Thr Leu Gly Val Glu Val Ser Asp Ser Ser Val Asn Cys Ile Glu
        195                 200                 205

Gln Thr Thr Glu Trp Thr Ala Cys Ser Lys Ser Cys Gly Met Gly Phe
    210                 215                 220

Ser Thr Arg Val Thr Asn Arg Asn Arg Gln Cys Glu Met Leu Lys Gln
225                 230                 235                 240

Thr Arg Leu Cys Met Val Arg Pro Cys Glu Gln Glu Pro Glu Gln Pro
                245                 250                 255

Thr Asp Lys Lys Gly Lys Lys Cys Leu Arg Thr Lys Lys Ser Leu Lys
            260                 265                 270

Ala Ile His Leu Gln Phe Lys Asn Cys Thr Ser Leu His Thr Tyr Lys
        275                 280                 285

Pro Arg Phe Cys Gly Val Cys Ser Asp Gly Arg Cys Cys Thr Pro His
    290                 295                 300

Asn Thr Lys Thr Ile Gln Ala Glu Phe Gln Cys Ser Pro Gly Gln Ile
305                 310                 315                 320

Val Lys Lys Pro Val Met Val Ile Gly Thr Cys Thr Cys His Thr Asn
                325                 330                 335

Cys Pro Lys Asn Asn Glu Ala Phe Leu Gln Glu Leu Glu Leu Lys Thr
            340                 345                 350

Thr Arg Gly Lys Met
        355

<210> SEQ ID NO 26
<211> LENGTH: 349
<212> TYPE: PRT
<213> ORGANISM: Homo sapiens

<400> SEQUENCE: 26

Met Thr Ala Ala Ser Met Gly Pro Val Arg Val Ala Phe Val Val Leu
1               5                   10                  15

Leu Ala Leu Cys Ser Arg Pro Ala Val Gly Gln Asn Cys Ser Gly Pro
            20                  25                  30

Cys Arg Cys Pro Asp Glu Pro Ala Pro Arg Cys Pro Ala Gly Val Ser
        35                  40                  45

Leu Val Leu Asp Gly Cys Gly Cys Cys Arg Val Cys Ala Lys Gln Leu
    50                  55                  60

Gly Glu Leu Cys Thr Glu Arg Asp Pro Cys Asp Pro His Lys Gly Leu
65                  70                  75                  80

Phe Cys Asp Phe Gly Ser Pro Ala Asn Arg Lys Ile Gly Val Cys Thr
                85                  90                  95

Ala Lys Asp Gly Ala Pro Cys Ile Phe Gly Gly Thr Val Tyr Arg Ser
            100                 105                 110
```

```
Gly Glu Ser Phe Gln Ser Ser Cys Lys Tyr Gln Cys Thr Cys Leu Asp
            115                 120                 125
Gly Ala Val Gly Cys Met Pro Leu Cys Ser Met Asp Val Arg Leu Pro
        130                 135                 140
Ser Pro Asp Cys Pro Phe Pro Arg Arg Val Lys Leu Pro Gly Lys Cys
145                 150                 155                 160
Cys Glu Glu Trp Val Cys Asp Glu Pro Lys Asp Gln Thr Val Val Gly
                165                 170                 175
Pro Ala Leu Ala Ala Tyr Arg Leu Glu Asp Thr Phe Gly Pro Asp Pro
            180                 185                 190
Thr Met Ile Arg Ala Asn Cys Leu Val Gln Thr Thr Glu Trp Ser Ala
        195                 200                 205
Cys Ser Lys Thr Cys Gly Met Gly Ile Ser Thr Arg Val Thr Asn Asp
210                 215                 220
Asn Ala Ser Cys Arg Leu Glu Lys Gln Ser Arg Leu Cys Met Val Arg
225                 230                 235                 240
Pro Cys Glu Ala Asp Leu Glu Glu Asn Ile Lys Lys Gly Lys Lys Cys
                245                 250                 255
Ile Arg Thr Pro Lys Ile Ser Lys Pro Ile Lys Phe Glu Leu Ser Gly
            260                 265                 270
Cys Thr Ser Met Lys Thr Tyr Arg Ala Lys Phe Cys Gly Val Cys Thr
        275                 280                 285
Asp Gly Arg Cys Cys Thr Pro His Arg Thr Thr Thr Leu Pro Val Glu
290                 295                 300
Phe Lys Cys Pro Asp Gly Glu Val Met Lys Lys Asn Met Met Phe Ile
305                 310                 315                 320
Lys Thr Cys Ala Cys His Tyr Asn Cys Pro Gly Asp Asn Asp Ile Phe
                325                 330                 335
Glu Ser Leu Tyr Tyr Arg Lys Met Tyr Gly Asp Met Ala
            340                 345

<210> SEQ ID NO 27
<211> LENGTH: 259
<212> TYPE: PRT
<213> ORGANISM: Homo sapiens

<400> SEQUENCE: 27

Met Ser Glu Val Pro Val Ala Arg Val Trp Leu Val Leu Leu Leu Leu
  1               5                  10                  15
Thr Val Gln Val Gly Val Thr Ala Gly Ala Pro Trp Gln Cys Ala Pro
            20                  25                  30
Cys Ser Ala Glu Lys Leu Ala Leu Cys Pro Pro Val Ser Ala Ser Cys
        35                  40                  45
Ser Glu Val Thr Arg Ser Ala Gly Cys Gly Cys Cys Pro Met Cys Ala
    50                  55                  60
Leu Pro Leu Gly Ala Ala Cys Gly Val Ala Thr Ala Arg Cys Ala Arg
65                  70                  75                  80
Gly Leu Ser Cys Arg Ala Leu Pro Gly Glu Gln Gln Pro Leu His Ala
                85                  90                  95
Leu Thr Arg Gly Gln Gly Ala Cys Val Gln Glu Ser Asp Ala Ser Ala
            100                 105                 110
Pro His Ala Ala Glu Ala Gly Ser Pro Glu Ser Pro Glu Ser Thr Glu
        115                 120                 125
Ile Thr Glu Glu Glu Leu Leu Asp Asn Phe His Leu Met Ala Pro Ser
```

```
                130              135              140
Glu Glu Asp His Ser Ile Leu Trp Asp Ala Ile Ser Thr Tyr Asp Gly
145                 150                 155                 160

Ser Lys Ala Leu His Val Thr Asn Ile Lys Lys Trp Lys Glu Pro Cys
                165                 170                 175

Arg Ile Glu Leu Tyr Arg Val Val Glu Ser Leu Ala Lys Ala Gln Glu
            180                 185                 190

Thr Ser Gly Glu Glu Ile Ser Lys Phe Tyr Leu Pro Asn Cys Asn Lys
        195                 200                 205

Asn Gly Phe Tyr His Ser Arg Gln Cys Glu Thr Ser Met Asp Gly Glu
    210                 215                 220

Ala Gly Leu Cys Trp Cys Val Tyr Pro Trp Asn Gly Lys Arg Ile Pro
225                 230                 235                 240

Gly Ser Pro Glu Ile Arg Gly Asp Pro Asn Cys Gln Ile Tyr Phe Asn
                245                 250                 255

Val Gln Asn

<210> SEQ ID NO 28
<211> LENGTH: 328
<212> TYPE: PRT
<213> ORGANISM: Homo sapiens

<400> SEQUENCE: 28

Met Leu Pro Arg Val Gly Cys Pro Ala Leu Pro Leu Pro Pro Pro Pro
1                   5                   10                  15

Leu Leu Pro Leu Leu Pro Leu Leu Leu Leu Leu Leu Gly Ala Ser Gly
                20                  25                  30

Gly Gly Gly Gly Ala Arg Ala Glu Val Leu Phe Arg Cys Pro Pro Cys
            35                  40                  45

Thr Pro Glu Arg Leu Ala Ala Cys Gly Pro Pro Pro Val Ala Pro Pro
        50                  55                  60

Ala Ala Val Ala Ala Val Ala Gly Gly Ala Arg Met Pro Cys Ala Glu
65                  70                  75                  80

Leu Val Arg Glu Pro Gly Cys Gly Cys Cys Ser Val Cys Ala Arg Leu
                85                  90                  95

Glu Gly Glu Ala Cys Gly Val Tyr Thr Pro Arg Cys Gly Gln Gly Leu
            100                 105                 110

Arg Cys Tyr Pro His Pro Gly Ser Glu Leu Pro Leu Gln Ala Leu Val
        115                 120                 125

Met Gly Glu Gly Thr Cys Glu Lys Arg Arg Asp Ala Glu Tyr Gly Ala
    130                 135                 140

Ser Pro Glu Gln Val Ala Asp Asn Gly Asp Asp His Ser Glu Gly Gly
145                 150                 155                 160

Leu Val Glu Asn His Val Asp Ser Thr Met Asn Met Leu Gly Gly Gly
                165                 170                 175

Gly Ser Ala Gly Arg Lys Pro Leu Lys Ser Gly Met Lys Glu Leu Ala
            180                 185                 190

Val Phe Arg Glu Lys Val Thr Glu Gln His Arg Gln Met Gly Lys Gly
        195                 200                 205

Gly Lys His His Leu Gly Leu Glu Glu Pro Lys Lys Leu Arg Pro Pro
    210                 215                 220

Pro Ala Arg Thr Pro Cys Gln Gln Glu Leu Asp Gln Val Leu Glu Arg
225                 230                 235                 240

Ile Ser Thr Met Arg Leu Pro Asp Glu Arg Gly Pro Leu Glu His Leu
```

```
                     245                 250                 255
Tyr Ser Leu His Ile Pro Asn Cys Asp Lys His Gly Leu Tyr Asn Leu
                260                 265                 270

Lys Gln Cys Lys Met Ser Leu Asn Gly Gln Arg Gly Glu Cys Trp Cys
            275                 280                 285

Val Asn Pro Asn Thr Gly Lys Leu Ile Gln Gly Ala Pro Thr Ile Arg
    290                 295                 300

Gly Asp Pro Glu Cys His Leu Phe Tyr Asn Glu Gln Gln Glu Ala Arg
305                 310                 315                 320

Gly Val His Thr Gln Arg Met Gln
                325

<210> SEQ ID NO 29
<211> LENGTH: 32
<212> TYPE: DNA
<213> ORGANISM: Artificial Sequence
<220> FEATURE:
<223> OTHER INFORMATION: oligonucleotide primer ZC 17948

<400> SEQUENCE: 29
cgtatcggcc ggccaccatg cagggctcc tc                              32

<210> SEQ ID NO 30
<211> LENGTH: 32
<212> TYPE: DNA
<213> ORGANISM: Artificial Sequence
<220> FEATURE:
<223> OTHER INFORMATION: oligonucleotide primer ZC 17949

<400> SEQUENCE: 30
cgcgcgggcg cgccttacag aatcttgagc tc                             32

<210> SEQ ID NO 31
<211> LENGTH: 25
<212> TYPE: DNA
<213> ORGANISM: Artificial Sequence
<220> FEATURE:
<223> OTHER INFORMATION: oligonucleotide primer ZC 17251

<400> SEQUENCE: 31
tctggacgtc ctcctgctgg tatag                                     25

<210> SEQ ID NO 32
<211> LENGTH: 25
<212> TYPE: DNA
<213> ORGANISM: Artificial Sequence
<220> FEATURE:
<223> OTHER INFORMATION: oligonucleotide primer ZC 17252

<400> SEQUENCE: 32
ggtatggagc aagggcaag ttggg                                      25

<210> SEQ ID NO 33
<211> LENGTH: 27
<212> TYPE: DNA
<213> ORGANISM: Artificial Sequence
<220> FEATURE:
<223> OTHER INFORMATION: oligonucleotide primer ZC 17156

<400> SEQUENCE: 33
gagtggcaac ttccagggcc aggagag                                   27

<210> SEQ ID NO 34
```

-continued

```
<211> LENGTH: 27
<212> TYPE: DNA
<213> ORGANISM: Artificial Sequence
<220> FEATURE:
<223> OTHER INFORMATION: oligonucleotide primer ZC 17157

<400> SEQUENCE: 34
cttttgctag cctcaaccct gactatc                                        27
```

NUCLEIC ACIDS ENCODING CONNECTIVE TISSUE GROWTH FACTOR HOMOLOGS

REFERENCE TO RELATED APPLICATIONS

This application is related to U.S. Patent Provisional Application No. 60/075,300, filed on Feb. 20, 1998, for which claims of benefit are made under 35 U.S.C. §119(e)(1).

BACKGROUND OF THE INVENTION

Connective tissue growth factor (CTGF) is a growth factor expressed by endothelial and fibroblastic cells. Two members of the CTGF family are known, CTGF (U.S. Pat. Nos. 5,585,270 and 5,408,040) and CTFG-2 (WO 96/01896), incorporated herein by reference. CTGF belongs to a family of growth factors that includes CTGF, CTGF-2, insulin binding proteins (IBP) 1 and 2. These growth factors have a cysteine-rich motif and several other structural protein domains in common, and have been demonstrated to have a role in cell proliferation, differentiation, and chemotaxis.

Studies have suggested that CTGF is immunologically similar to PDGF, with PDGF antibodies from both A and B chains binding to CTGF (Bradham et al., *J. of Cell Biol.* 114 (6):1285–1294, 1991), and it has been reported that biological activity of CTGF can be blocked using these antibodies.

It has recently been demonstrated that porcine CTGF isolated from uterus is mitogenic for fibroblasts and smooth muscle cells but not endothelial cells. In addition, a N-terminally truncated form of the protein was active as well (Brigstock et al., *J. Biol. Chem.* 272:20275–20282, 1997). It has been suggested that this protein could play a role in the growth and remodeling of the endometrium and placenta.

The CTGF family is believed to play a role production of the extracellular matrix components, such as collagen and fibronectin. Collagen and fibronectin are components of many connective tissues, e.g., ligaments, cartilage, tendons and vessel walls. Current therapy for ligament repair is limited to immobilising the damaged tissue, i.e., stapling, or replacing the damaged tissue with synthetic or natural grafts. These tissues are notoriously difficult to heal, even in healthy individuals, and compositions that would improve recovery time would be very valuable.

The present invention is directed to novel polypeptides and polynucleotides encoding the polypeptide that show predominantly high expression in testis, trachea and bone marrow, thus providing a new molecule for regulating growth, differentiation, chemotaxis and induction of specialized cell functions in these tissues.

SUMMARY OF THE INVENTION

It is an object of the present invention to provide an isolated polynucleotide molecule comprising a polynucleotide sequence that encodes a connective tissue growth factor homolog polypeptide that is at least 70% identical to the amino acid sequence as shown in SEQ ID NO: 2 from residue 24 to residue 354.

In another embodiment, the present invention provides for a polynucleotide molecule wherein the polynucleotide molecule comprises a region having the following motif as shown in SEQ ID NO: 23:

Cx{8,10}CxCCxxCx{7}Cx{5,6}Cx{5,7}Cx{12,13}Cx{7,8}Cx{20}CxCx{6}Cx{12,14}Cx{13,17}C wherein x{ } is the number of amino acid residues between cysteines (C).

In another embodiment, the polynucleotide is 80% or 90% identical to the amino acid sequence as shown in SEQ ID NO: 2 from residue 24 to residue 354.

It is also the object of the present invention to provide an isolated polynucleotide acid molecule that encodes a connective tissue growth factor homolog polypeptide, wherein the polynucleotide molecule is selected from the group consisting of (a) a molecules having the nucleotide sequence of SEQ ID NO:1 from nucleotide 17 or 86 to nucleotide 1078, (b) a molecule encoding the amino acid sequence of SEQ ID NO:3 from nucleotide 1 or 70 to nucleotide 1062, and (c) a molecule that hybridizes under stringent wash conditions to a polynucleotide molecule having the nucleotide sequence of nucleotides 86 to 1078 of SEQ ID NO:1, or the complement of nucleotides 86 to 1078 of SEQ ID NO:1.

In another embodiment, the differences in the amino acid sequence encoded by the polynucleotide and SEQ ID NO: 2 are conservative amino acid changes.

In other aspects, the present invention provides an expression vector comprising the following operably linked elements: a transcription promoter; a DNA segment comprising the isolated polynucleotide sequence that encodes a connective tissue growth factor homolog polypeptide that is at least 70% identical to the amino acid sequence as shown in SEQ ID NO: 2 from residue 24 to residue 354; and a transcription terminator and a cultured host cell into which has been introduced the expression vector.

In another embodiment, the present invention provides a method of producing a connective tissue growth factor homolog polypeptide comprising: (a) culturing the host cells of expressing the CTGF homolog polypeptide; and (b) isolating the connective tissue growth factor homolog polypeptide from the cultured host cells.

In another aspect, the present invention provides an isolated connective tissue growth factor polypeptide comprising an amino acid sequence that is at least 70% identical to the amino acid sequence as shown in SEQ ID NO: 2 from residue 24 to residue 354.

In other embodiments, the present invention provides CTGF homolog polypeptides wherein the amino acid sequence is at least 80% or 90% identical.

In another embodiment, the CTGF homolog polypeptide molecule comprises a region having the following motif as shown in SEQ ID NO: 23:

Cx{8,10}CxCCxxCx{7}Cx{5,6}Cx{5,7}Cx{12,13}Cx{7,8}Cx{20}CxCx{6}Cx{12,14}Cx{13,17}C wherein x{ } is the number of amino acid residues between cysteines (C).

In another aspect, the present invention provides an antibody or antibody fragment that specifically binds with the CTGF homolog polypeptide.

In another aspect, the present invention provides a method of detecting the presence of connective tissue growth factor homolog polypeptide in a biological sample, comprising the steps of: (a) contacting the biological sample with an antibody, or an antibody fragment of claim 14, wherein the contacting is performed under conditions that allow the binding of the antibody or antibody fragment to the biological sample, and (b) detecting any of the bound antibody or bound antibody fragment.

In another aspect, the present invention provides an anti-idiotype antibody, or anti-idiotype antibody fragment, that specifically binds with the antibody or antibody fragment.

In another aspect, the present invention provides a method of detecting a chromosome 6q abnormality in sample from an individual comprising: (a) obtaining zCTGF4 RNA from the sample; (b) generating zCTGF4 cDNA by polymerase chain reaction; and (c) comparing the nucleic acid sequence of the zCTGF4 cDNA to the nucleic acid sequence as shown in SEQ ID NO: 1.

In another embodiment, the present invention provides that the difference between the sequence of the zCTGF4 cDNA or zCTGF4 gene in the sample and the zCTGF4 sequence as shown in SEQ ID NO: 1 is indicative of chromosome 6q abnormality.

BRIEF DESCRIPTION OF THE DRAWINGS

FIG. 1 illustrates a multiple alignment of human zCTGF4 (SEQ ID NO: 2) and other members of the connective tissue growth factor family that includes, mouse zCTGF2 (SEQ ID NO: 5), human NOV (NOV HU; SEQ ID NO: 25), human CTGF1 (CTGF H; SEQ ID NO: 26), human insulin binding protein 1 (IBP1 H; SEQ ID NO: 27), and human insulin binding protein 2 (IBP2 H; SEQ ID NO: 28).

DETAILED DESCRIPTION OF THE INVENTION

Prior to setting forth the invention in detail, it may be helpful to the understanding thereof to define the following terms:

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952–4, 1985), substance P, Flag™ peptide (Hopp et al., *Biotechnology* 6:1204–10, 1988), streptavidin binding peptide, or other antigenic epitope or binding domain. See, in general, Ford et al., *Protein Expression and Purification* 2: 95–107, 1991. DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

The term "complements of a polynucleotide molecule" denotes a polynucleotide molecule having a complementary base sequence and reverse orientation as compared to a reference sequence. For example, the sequence 5' ATG-CACGGG 3' is complementary to 5' CCCGTGCAT 3'.

The term "contig" denotes a polynucleotide that has a contiguous stretch of identical or complementary sequence to another polynucleotide. Contiguous sequences are said to "overlap" a given stretch of polynucleotide sequence either in their entirety or along a partial stretch of the polynucleotide.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "operably linked", when referring to DNA segments, indicates that the segments are arranged so that they function in concert for their intended purposes, e.g., transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-peptide structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention is based in part upon the discovery of a novel DNA sequence that encodes a connective tissue growth factor homolog polypeptide, i.e., polypeptides having homology to other members of a family of growth factors that are secreted and contain a cysteine motif of the formula:

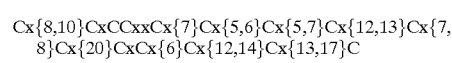

wherein x{ } is the number of amino acid residues between cysteines (C) as shown in SEQ ID NO: 23. This motif represents a consecutive domain arrangement known as a insulin-like growth factor binding domain followed by a Von Willebrand Factor c (VWFc) domain (Bork, *FEBS Letts.* 327:125–130, 1993). The protein domain arrangement is unique to the CTGF/NOV protein structure family. The insulin-like growth factor binding domain is represented by the motif:

wherein x{ } is the number of amino acid residues between cysteines (C) as shown in SEQ ID NO: 24. This pattern is found in all known members of the connective tissue growth factors and insulin binding protein family (for example: human CTGF, human CTGF-2, human NOV, human IBPs 1 and 2), and is unique to these proteins.

Analysis of the tissue distribution of the mRNA corresponding to this novel DNA showed that expression was highest in testis, followed by apparent but decreased expression levels in trachea, bone marrow and kidney tissue. The connective tissue growth factor homolog polypeptide has been designated zCTGF4.

The ortholog from mouse has also been identified and designated zCTGF2. A DNA sequence and corresponding putative amino acid sequence are shown in SEQ ID NOS: 4 and 5, respectively.

The novel zCTGF4 polypeptides of the present invention were initially identified by querying an EST database for homologous sequences to connective tissue growth factor and insulin-binding proteins. A single EST sequence was discovered and predicted to be related to the connective tissue growth factor family. Sequence analysis of the clone from which the EST was derived revealed that the clone contained a defective cDNA with incorrect sequence. Isolation of an independent clone from a testis library revealed that the original cDNA clone contained intronic sequence at the 5' end of the EST. The nucleotide sequence is described in SEQ ID NO. 1 from nucleotide 17 to nucleotide 1078, and its deduced amino acid sequence is described in SEQ ID NO. 2.

Analysis of the DNA encoding a zCTGF4 polypeptide (SEQ ID NO: 1) revealed an open reading frame encoding 354 amino acids (SEQ ID NO: 2) comprising a secretory signal peptide of 23 amino acid residues (residue 1 (Met) to residue 23 (Gly) of SEQ ID NO: 2) and a mature polypeptide of 331 amino acids (residue 24 (Thr) to residue 354 (Leu) of SEQ ID NO: 2). An alternatively spliced variant has a 16 amino acid secretory signal peptide (residue 1 (Met) to residue 16 (Gly) of SEQ ID NO: 2, and a mature polypeptide of 338 amino acid residues (residue 17 (Phe) to residue 354 (Leu) of SEQ ID NO: 2).

CTGF family members are characterized by a multidomain structure comprising a IBP domain (amino acid residue 59 (Pro) to 102 (Tyr) of SEQ ID NO: 2) that has been suggested as an insulin growth factor binding domain (Kiefer et al., *J. Biol. Chem.* 266:9043–9049, 1991), a von Willebrand factor c domain (amino acid residue 114 (Cys) to 179 (Cys) of SEQ ID NO: 2) that may be involved in multimerization, a variable domain (amino acid 180 (Ser) to 208 (Lys), that may be involved in tissue, matrix, growth factor or receptor specific interactions; and a sulfated glycoconjugate binding motif domain (amino acid residue 209 (Cys) to 252 (Cys) of SEQ ID NO: 2) that is thought to be involved in binding large macromolecules (Holt et al., *J. Biol. Chem.* 265:2852–2855, 1990).

CTGF has recently been demonstrated to bind IGF at low affinity (Kim et al., *Proc. Nat. Acad. Sci.* 94:12981–12986, 1997), and thereby expands the insulin-like growth factor binding protein (IGFBP) superfamily to include the CTGFs. The superfamily of IGFBPs now comprises both proteins that bind IGF high affinity (e.g., IGFBP 1–5) and proteins that bind IGF with low affinity (nov, cyr61 and CTGF), suggesting proteins affect cell growth in both IGF-dependent and IGF-independent manners. The IGF binding potential of members of the CTGF family, including zCTGF4, may act as a competitive inhibitor of the biologically free component of IGF. ZCTGF4 may affect other pathways that IGFBPs play a role in, for example, competing with endogenous IGFBP for proteases that degrade the IGF/IGFBP complex, resulting in changes in the circulating levels of IGF.

A multiple alignment, as shown in FIG. 1, also revealed that zCTGF4, like several other known members of the CTGF family, has a heparin binding domain that has been suggested as a receptor binding and dimerization domain. The heparin binding domain is shown in SEQ ID NO: 2 from residue 262 (Ile) to residue 295 (Phe). The domain structure has been reviewed by Brigstock et al., ibid., 1997 and Bork, *FEBS Letts.* 327:125–130, 1993, both incorporated herein by reference.

It is generally believed that under selective pressure for organisms to acquire new biological functions, new CTGF family members arose from duplication of existing genes leading to the existence of multi-gene families. Family members thus contain vestiges of the ancestral gene, and these characteristic features can be exploited in the isolation and identification of additional family members. It has recently been demonstrated that N-terminally truncated CTGF molecules isolated from uterine secretory fluids have mitogenic activity and will bind heparin (Brigstock et al., ibid., 1997), and may have activity. An N-terminally truncated zCTGF4 molecule would be expected to have similar activity, and would comprise molecules without the IBP domain and may or may not be C-terminally truncated as well.

SEQ ID NO: 3 is a degenerate polynucleotide sequence that encompasses all polynucleotides that could encode the zCTGF4 polypeptide of SEQ ID NO: 2 (amino acids 1 or 24 to 354). Thus, zCTGF4 polypeptide-encoding polynucleotides ranging from nucleotide 17 or 85 to nucleotide 1078 of SEQ ID NO: 2 or nucleotide 1 or 69 to 1062 of SEQ ID NO: 3 are contemplated by the present invention. Also contemplated by the present invention are fragments and fusions as described herein with respect to SEQ ID NO: 1, which are formed from analogous regions of SEQ ID NO: 3, wherein nucleotides 191 to 322 of SEQ ID NO: 1 correspond to nucleotides 175 to 306 of SEQ ID NO: 3, for the IBP domain; wherein nucleotides 356 to 553 of SEQ ID NO: 1 correspond to nucleotides 340 to 537 of SEQ ID NO: 3, for the von Willebrand factor (VWFc) domain; wherein nucleotides 554 to 640 of SEQ ID NO: 1 correspond to nucleotides 538 to 624 of SEQ ID NO: 3 for the variable region; wherein nucleotides 641 to 772 of SEQ ID NO: 1 correspond to nucleotides 625 to 756 of SEQ ID NO: 3, for the sulfated glycoconjugate binding domain; and wherein nucleotide 800 to nucleotide 904 of SEQ ID NO: 1 correspond to nucleotide 784 to nucleotide 888 of SEQ ID NO: 3 for the heparin binding domain. Table 1 sets forth the one-letter codes used within SEQ ID NO: 3 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 1

| Nucleotide | Resolution | Complement | Resolution |
| --- | --- | --- | --- |
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NOS: 2 and 5, encompassing all possible codons for a given amino acid, are set forth in Table 2.

TABLE 2

| Amino Acid | One Letter Code | Codons | | | | | | Degenerate Codon |
|---|---|---|---|---|---|---|---|---|
| Cys | C | TGC | TGT | | | | | TGY |
| Ser | S | AGC | AGT | TCA | TCC | TCG | TCT | WSN |
| Thr | T | ACA | ACC | ACG | ACT | | | ACN |
| Pro | P | CCA | CCC | CCG | CCT | | | CCN |
| Ala | A | GCA | GCC | GCG | GCT | | | GCN |
| Gly | G | GGA | GGC | GGG | GGT | | | GGN |
| Asn | N | AAC | AAT | | | | | AAY |
| Asp | D | GAC | GAT | | | | | GAY |
| Glu | E | GAA | GAG | | | | | GAR |
| Gln | Q | CAA | CAG | | | | | CAR |
| His | H | CAC | CAT | | | | | CAY |
| Arg | R | AGA | AGG | CGA | CGC | CGG | CGT | MGN |
| Lys | K | AAA | AAG | | | | | AAR |
| Met | M | ATG | | | | | | ATG |
| Ile | I | ATA | ATC | ATT | | | | ATH |
| Leu | L | CTA | CTC | CTG | CTT | TTA | TTG | YTN |
| Val | V | GTA | GTC | GTG | GTT | | | GTN |
| Phe | F | TTC | TTT | | | | | TTY |
| Tyr | Y | TAC | TAT | | | | | TAY |
| Trp | W | TGG | | | | | | TGG |
| Ter | | TAA | TAG | TGA | | | | TRR |
| Asn\|Asp | B | | | | | | | RAY |
| Glu\|Gln | Z | | | | | | | SAR |
| Any | X | | | | | | | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NOS: 2 and 5. Variant sequences can be readily tested for functionality as described herein.

One of ordinary skill in the art will also appreciate that different species can exhibit "preferential codon usage." In general, see, Grantham, et al., *Nuc. Acids Res.,* 8:1893–912, 1980; Haas, et al. *Curr. Biol.,* 6:315–24, 1996; Wain-Hobson, et al., *Gene,* 13:355–64, 1981; Grosjean and Fiers, *Gene,* 18:199–209, 1982; Holm, *Nuc. Acids Res.,* 14:3075–87, 1986; Ikemura, *J. Mol. Biol.,* 158:573–97, 1982. As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid Threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequence disclosed in SEQ ID NO: 3 serves as a template for optimizing expression of polynucleotides in various cell types and species commonly used in the art and disclosed herein. Sequences containing preferential codons can be tested and optimized for expression in various species, and tested for functionality as disclosed herein.

The present invention further provides variant polypeptides and nucleic acid molecules that represent counterparts from other species (orthologs). These species include, but are not limited to mammalian, avian, amphibian, reptile, fish, insect and other vertebrate and invertebrate species. Of particular interest are zCTGF4 polypeptides from other mammalian species, including murine, porcine, ovine, bovine, canine, feline, equine, and other primate polypeptides. Orthologs of human zCTGF4 can be cloned using information and compositions provided by the present invention in combination with conventional cloning techniques. For example, a cDNA can be cloned using mRNA obtained from a tissue or cell type that expresses zCTGF4 as disclosed herein. Suitable sources of mRNA can be identified by probing northern blots with probes designed from the sequences disclosed herein. A library is then prepared from mRNA of a positive tissue or cell line. The mouse sequence ZCTGF2 is a representative ortholog of the human connective tissue growth factor, zCTGF4, and is disclosed herein as SEQ ID NOS: 4 and 5.

An zCTGF4-encoding cDNA can then be isolated by a variety of methods, such as by probing with a complete or partial human cDNA or with one or more sets of degenerate probes based on the disclosed sequences. A cDNA can also be cloned using the polymerase chain reaction with primers designed from the representative human zCTGF4 sequences disclosed herein. Within an additional method, the cDNA library can be used to transform or transfect host cells, and expression of the cDNA of interest can be detected with an antibody to zCTGF4 polypeptide. Similar techniques can also be applied to the isolation of genomic clones.

The present invention provides polynucleotide molecules including DNA and RNA molecules that encode the zCTGF4 polypeptides disclosed above.

ZCTGF4 polynucleotide sequences disclosed herein can also be used as probes or primers to clone 5' non-coding regions of a zCTGF4 gene. In view of the tissue-specific expression observed for zCTGF4 by Northern blotting, this gene region is expected to provide for testis-, trachea-, bone marrow-, and kidney-specific expression. Promoter elements from a zCTGF4 gene could thus be used to direct the tissue-specific expression of heterologous genes in, for example, transgenic animals or patients treated with gene therapy. Cloning of 5' flanking sequences also facilitates production of zCTGF4 proteins by "gene activation" as disclosed in U.S. Pat. No. 5,641,670. Briefly, expression of an endogenous ZCTGF4 gene in a cell is altered by introducing into the zCTGF4 locus a DNA construct comprising at least a targeting sequence, a regulatory sequence, an exon, and an unpaired splice donor site. The targeting sequence is a zCTGF4 5' non-coding sequence that permits homologous recombination of the construct with the endogenous zCTGF4 locus, whereby the sequences within the construct become operably linked with the endogenous zCTGF4 coding sequence. In this way, an endogenous zCTGF4 promoter can be replaced or supplemented with other regulatory sequences to provide enhanced, tissue-specific, or otherwise regulated expression.

Those skilled in the art will recognize that the sequence disclosed in SEQ ID NO:1 represents a single allele of human zCTGF4 and that allelic variation and alternative splicing are expected to occur. Allelic variants of this sequence can be cloned by probing cDNA or genomic libraries from different individuals according to standard procedures. Allelic variants of the nucleotide sequence shown in SEQ ID NO:1, including those containing silent mutations and those in which mutations result in amino acid sequence changes, are within the scope of the present invention, as are proteins which are allelic variants of SEQ ID NO:2. cDNA molecules generated from alternatively spliced mRNAs, which retain the properties of the zCTGF4 polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

The present invention provides methods for using zCTGF4 polynucleotides and polypeptides to diagnose chromosomal disorders associated with abnormal expression of the zCTGF4 protein. Detectable chromosomal mutations at the zCTGF4 gene locus include, but are not limited to, aneuploidy, gene copy number changes, insertions, deletions, restriction site changes and rearrangements. Such aberrations can be identified by employing molecular genetic techniques, such as restriction fragment length polymorphism (RFLP) analysis, short tandem repeat (STR) analysis employing PCR techniques, and other genetic linkage analysis techniques known in the art (Molecular Cloning: *A Laboratory Manual,* 2nd ed., Cold Spring Harbor Laboratory Press, Cold Spring Harbor, N.Y., 1989, and Ausubel et al., eds., *Current Protocols in Molecular Biology,* John Wiley and Sons, Inc., NY, 1987; A. J. Marian, *Chest* 108:255–65, 1995). Analyses of DNA samples can detect deletions and insertions by changes in size in amplified DNA products by comparing a sample DNA to a normal zCTGF4 DNA standard. Mismatches in duplex DNA can be detected by RNase digestion or differences in melting temperature. Other methods for detecting differences in sequences include, changes electrophoretic motility, Southern analysis, and direct DNA sequencing. Recently, techniques for accessing genetic information with high-density arrays have been available (Chee et al., *Science* 274:610–614, 1996), and can analyze large fragments of genomic DNA with high resolution.

Analysis of chromosomal DNA using the zCTGF4 polynucleotide sequence is useful for correlating disease with abnormalities localized to chromosome 6. The zCTGF4 gene has been localized to chromosome 6q22.1. Studies of the DNA sequences, cDNA and/or genomic DNA, of some of the individuals presenting disease that contain a mutation in the sequence of the zCTGF4 gene, that is not present in normal individuals, can provide strong evidence for the mutation as causative of the disease. In one embodiment, the methods of the present invention provide a method of detecting a chromosome 6q abnormality in sample from an individual comprising: (a) obtaining zCTGF4 RNA from the sample; (b) generating zCTGF4 cDNA by polymerase chain reaction; and (c) comparing the nucleic acid sequence of the zCTGF4 cDNA to the nucleic acid sequence as shown in SEQ ID NO: 1. In further embodiments, the difference between the sequence of the zCTGF4 cDNA or zCTGF4 gene in the sample and the zCTGF4 sequence as shown in SEQ ID NO: 1 is indicative of chromosome 6q abnormality.

Within preferred embodiments of the invention, the isolated nucleic acid molecules can hybridize under stringent conditions to nucleic acid molecules having the nucleotide sequence of SEQ ID NO:1, to nucleic acid molecules having the nucleotide sequence of nucleotides 86 to 1078 of SEQ ID NO:1, or to nucleic acid molecules having a nucleotide sequence complementary to SEQ ID NO:1. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe.

A pair of nucleic acid molecules, such as DNA-DNA, RNA-RNA and DNA-RNA, can hybridize if the nucleotide sequences have some degree of complementarity. Hybrids can tolerate mismatched base pairs in the double helix, but the stability of the hybrid is influenced by the degree of mismatch. The Tm of the mismatched hybrid decreases by 1° C. for every 1–1.5% base pair mismatch. Varying the stringency of the hybridization conditions allows control over the degree of mismatch that will be present in the hybrid. The degree of stringency increases as the hybridization temperature increases and the ionic strength of the hybridization buffer decreases. Stringent hybridization conditions encompass temperatures of about 5–25° C. below the $T_m$ of the hybrid and a hybridization buffer having up to 1 M $Na^+$. Higher degrees of stringency at lower temperatures can be achieved with the addition of formamide which reduces the Tm of the hybrid about 1° C. for each 1% formamide in the buffer solution. Generally, such stringent conditions include temperatures of 20–70° C. and a hybridization buffer containing up to 6×SSC and 0–50% formamide. A higher degree of stringency can be achieved at temperatures of from 40–70° C. with a hybridization buffer having up to 4×SSC and from 0–50% formamide. Highly stringent conditions typically encompass temperatures of 42–70° C. with a hybridization buffer having up to 1×SSC and 0–50% formamide. Different degrees of stringency can be used during hybridization and washing to achieve maximum specific binding to the target sequence. Typically, the washes following hybridization are performed at increasing degrees of stringency to remove non-hybridized polynucleotide probes from hybridized complexes.

The above conditions are meant to serve as a guide and it is well within the abilities of one skilled in the art to adapt these conditions for use with a particular polypeptide hybrid. The $T_m$ for a specific target sequence is the temperature (under defined conditions) at which 50% of the target sequence will hybridize to a perfectly matched probe sequence. Those conditions which influence the $T_m$ include, the size and base pair content of the polynucleotide probe, the ionic strength of the hybridization solution, and the presence of destabilizing agents in the hybridization solution. Numerous equations for calculating $T_m$ are known in the art, and are specific for DNA, RNA and DNA-RNA hybrids and polynucleotide probe sequences of varying length (see, for example, Sambrook et al., *Molecular Cloning: A Laboratory Manual,* Second Edition (Cold Spring Harbor Press 1989); Ausubel et al., (eds.), *Current Protocols in Molecular Biology* (John Wiley and Sons, Inc. 1987); Berger and Kimmel (eds.), *Guide to Molecular Cloning Techniques,* (Academic Press, Inc. 1987); and Wetmur, *Crit. Rev. Biochem. Mol. Biol.* 26:227 (1990)). Sequence analysis software such as OLIGO 6.0 (LSR; Long Lake, Minn.) and Primer Premier 4.0 (Premier Biosoft International; Palo Alto, Calif.), as well as sites on the Internet, are available tools for analyzing a given sequence and calculating $T_m$ based on user defined criteria. Such programs can also analyze a given sequence under defined conditions and identify suitable probe sequences. Typically, hybridization of longer polynucleotide sequences, >50 base pairs, is performed at temperatures of about 20–25° C. below the calculated $T_m$. For smaller probes, <50 base pairs, hybridization is typically carried out at the $T_m$ or 5–10° C. below.

This allows for the maximum rate of hybridization for DNA-DNA and DNA-RNA hybrids.

The length of the polynucleotide sequence influences the rate and stability of hybrid formation. Smaller probe sequences, <50 base pairs, reach equilibrium with complementary sequences rapidly, but may form less stable hybrids. Incubation times of anywhere from minutes to hours can be used to achieve hybrid formation. Longer probe sequences come to equilibrium more slowly, but form more stable complexes even at lower temperatures. Incubations are allowed to proceed overnight or longer. Generally, incubations are carried out for a period equal to three times the calculated Cot time. Cot time, the time it takes for the polynucleotide sequences to reassociate, can be calculated for a particular sequence by methods known in the art.

The base pair composition of polynucleotide sequence will effect the thermal stability of the hybrid complex, thereby influencing the choice of hybridization temperature and the ionic strength of the hybridization buffer. A-T pairs are less stable than G-C pairs in aqueous solutions containing sodium chloride. Therefore, the higher the G-C content, the more stable the hybrid. Even distribution of G and C residues within the sequence also contribute positively to hybrid stability. In addition, the base pair composition can be manipulated to alter the $T_m$ of a given sequence. For example, 5-methyldeoxycytidine can be substituted for deoxycytidine and 5-bromodeoxyuridine can be substituted for thymidine to increase the $T_m$, whereas 7-deazz-2'-deoxyguanosine can be substituted for guanosine to reduce dependence on $T_m$.

The ionic concentration of the hybridization buffer also affects the stability of the hybrid. Hybridization buffers generally contain blocking agents such as Denhardt's solution (Sigma Chemical Co., St. Louis, Mo.), denatured salmon sperm DNA, tRNA, milk powders (BLOTTO), heparin or SDS, and a $Na^+$ source, such as SSC (1×SSC: 0.15 M sodium chloride, 15 mM sodium citrate) or SSPE (1×SSPE: 1.8 M NaCl, 10 mM $NaH_2PO_4$, 1 mM EDTA, pH 7.7). By decreasing the ionic concentration of the buffer, the stability of the hybrid is increased. Typically, hybridization buffers contain from between 10 mM–1 M $Na^+$. The addition of destabilizing or denaturing agents such as formamide, tetralkylammonium salts, guanidinium cations or thiocyanate cations to the hybridization solution will alter the $T_m$ of a hybrid. Typically, formamide is used at a concentration of up to 50% to allow incubations to be carried out at more convenient and lower temperatures. Formamide also acts to reduce non-specific background when using RNA probes.

As an illustration, a nucleic acid molecule encoding a variant zCTGF4 polypeptide can be hybridized with a nucleic acid molecule having the nucleotide sequence of SEQ ID NO:1 (or its complement) at 42° C. overnight in a solution comprising 50% formamide, 5×SSC (1×SSC: 0.15 M sodium chloride and 15 mM sodium citrate), 50 mM sodium phosphate (pH 7.6), 5×Denhardt's solution (100× Denhardt's solution: 2% (w/v) Ficoll 400, 2% (w/v) polyvinylpyrrolidone, and 2% (w/v) bovine serum albumin), 10% dextran sulfate, and 20 µg/ml denatured, sheared salmon sperm DNA. One of skill in the art can devise variations of these hybridization conditions. For example, the hybridization mixture can be incubated at a higher temperature, such as about 65° C., in a solution that does not contain formamide. Moreover, premixed hybridization solutions are available (e.g., EXPRESSHYB Hybridization Solution from CLONTECH Laboratories, Inc.), and hybridization can be performed according to the manufacturer's instructions.

Following hybridization, the nucleic acid molecules can be washed to remove non-hybridized nucleic acid molecules under stringent conditions, or under highly stringent conditions. Typical stringent washing conditions include washing in a solution of 0.5×–2×SSC with 0.1% sodium dodecyl sulfate (SDS) at 55–65° C. That is, nucleic acid molecules encoding a variant zCTGF4 polypeptide hybridize with a nucleic acid molecule having the nucleotide sequence of SEQ ID NO:1 (or its complement) under stringent washing conditions, in which the wash stringency is equivalent to 0.5×–2×SSC with 0.1% SDS at 55–65° C., including 0.5× SSC with 0.1% SDS at 55° C., or 2×SSC with 0.1% SDS at 65° C. One of skill in the art can readily devise equivalent conditions, for example, by substituting SSPE for SSC in the wash solution.

Typical highly stringent washing conditions include washing in a solution of 0.1×–0.2×SSC with 0.1% sodium dodecyl sulfate (SDS) at 50–65° C. In other words, nucleic acid molecules encoding a variant zCTGF4 polypeptide hybridize with a nucleic acid molecule having the nucleotide sequence of SEQ ID NO:1 (or its complement) under highly stringent washing conditions, in which the wash stringency is equivalent to 0.1×–0.2×SSC with 0.1% SDS at 50–65° C., including 0.1×SSC with 0.1% SDS at 50° C., or 0.2×SSC with 0.1% SDS at 65° C.

The present invention also provides isolated zCTGF4 polypeptides that have a substantially similar sequence identity to the polypeptides of SEQ ID NO:2, or their orthologs. The term "substantially similar sequence identity" is used herein to denote polypeptides comprising at least 70%, at least 80%, at least 90%, at least 95% or greater than 95% sequence identity to the sequences shown in SEQ ID NO:2, or their orthologs. The present invention also includes polypeptides that comprise an amino acid sequence having at least 70%, at least 80%, at least 90%, at least 95% or greater than 95% sequence identity to the sequence of amino acid residues 1 or 24 to 354 of SEQ ID NO:2. The present invention further includes nucleic acid molecules that encode such polypeptides. Methods for determining percent identity are described below.

The present invention also contemplates zCTGF4 variant nucleic acid molecules that can be identified using two criteria: a determination of the similarity between the encoded polypeptide with the amino acid sequence of SEQ ID NO:2, and/or a hybridization assay, as described above. Such zCTGF4 variants include nucleic acid molecules (1) that hybridize with a nucleic acid molecule having the nucleotide sequence of SEQ ID NO:1 (or its complement) under stringent washing conditions, in which the wash stringency is equivalent to 0.5×–2×SSC with 0.1% SDS at 55–65° C., or (2) that encode a polypeptide having at least 70%, at least 80%, at least 90%, at least 95% or greater than 95% sequence identity to the amino acid sequence of SEQ ID NO:2. Alternatively, zCTGF4 variants can be characterized as nucleic acid molecules (1) that hybridize with a nucleic acid molecule having the nucleotide sequence of SEQ ID NO:1 (or its complement) under highly stringent washing conditions, in which the wash stringency is equivalent to 0.1×–0.2×SSC with 0.1% SDS at 50–65° C., and (2) that encode a polypeptide having at least 70%, at least 80%, at least 90%, at least 95% or greater than 95% sequence identity to the amino acid sequence of SEQ ID NO:2.

Percent sequence identity is determined by conventional methods. See, for example, Altschul et al., *Bull. Math. Bio.* 48:603 (1986), and Henikoff and Henikoff, *Proc. Natl. Acad. Sci. USA* 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.) as shown in Table 3 (amino acids are indicated by the standard one-letter codes).

$$\frac{\text{Total number of identical matches}}{\text{[length of the longer sequence plus the number of gaps introduced into the longer sequence in order to align the two sequences]}} \times 100$$

TABLE 3

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant zCTGF4. The FASTA algorithm is described by Pearson and Lipman, Proc. Nat'l Acad. Sci. USA 85:2444 (1988), and by Pearson, Meth. Enzymol. 183:63 (1990).

Briefly, FASTA first characterizes sequence similarity by identifying regions shared by the query sequence (e.g., SEQ ID NO:2) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, J. Mol. Biol. 48:444 (1970); Sellers, SIAM J. Appl. Math. 26:787 (1974)), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, Meth. Enzymol. 183:63 (1990).

FASTA can also be used to determine the sequence identity of nucleic acid molecules using a ratio as disclosed above. For nucleotide sequence comparisons, the ktup value can range between one to six, preferably from four to six.

Variant zCTGF4 polypeptides or polypeptides with substantially similar sequence identity are characterized as having one or more amino acid substitutions, deletions or additions. These changes are preferably of a minor nature, that is conservative amino acid substitutions (see Table 4) and other substitutions that do not significantly affect the folding or activity of the polypeptide; small deletions, typically of one to about 30 amino acids; and amino- or carboxyl-terminal extensions, such as an amino-terminal methionine residue, a small linker peptide of up to about 20–25 residues, or an affinity tag. The present invention thus includes polypeptides of from about 28 to 354 amino acid residues that comprise a sequence that is at least 70%, preferably at least 90%, and more preferably 95% or more identical to the corresponding region of SEQ ID NO:2. In particular, peptides and polypeptides corresponding to domains of the zCTGF4 molecules as shown in SEQ ID NO: 2 include the IBP domain (residues 59–102), the von Willebrand factor C domain (residues 114–179), the variable domain (residues 180–208) and the glycoconjugate binding domains (residues 209–252) are within the scope of the present invention. Polypeptides comprising affinity tags can further comprise a proteolytic cleavage site between the zCTGF4 polypeptide and the affinity tag. Preferred such sites include thrombin cleavage sites and factor Xa cleavage sites.

TABLE 4

| Conservative amino acid substitutions | |
|---|---|
| Basic: | arginine |
| | lysine |
| | histidine |
| Acidic: | glutamic acid |
| | aspartic acid |

TABLE 4-continued

Conservative amino acid substitutions

| | |
|---|---|
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is typically carried out in a cell-free system comprising an *E. coli* S30 extract and commercially available enzymes and other reagents. Proteins are purified by chromatography. See, for example, Robertson et al., *J. Am. Chem. Soc.* 113:2722 (1991), Ellman et al., *Methods Enzymol.* 202:301 (1991), Chung et al., *Science* 259:806 (1993), and Chung et al., *Proc. Nat'l Acad. Sci. USA* 90:10145 (1993).

In a second method, translation is carried out in Xenopus oocytes by microinjection of mutated mRNA and chemically aminoacylated suppressor tRNAs (Turcatti et al., *J. Biol. Chem.* 271:19991 (1996)). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470 (1994). Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395 (1993)).

A limited number of non-conservative amino acids, amino acids that are not encoded by the genetic code, non-naturally occurring amino acids, and unnatural amino acids may be substituted for zCTGF4 amino acid residues.

Multiple amino acid substitutions can be made and tested using known methods of mutagenesis and screening, such as those disclosed by Reidhaar-Olson and Sauer (*Science* 241:53 (1988)) or Bowie and Sauer (*Proc. Nat'l Acad. Sci. USA* 86:2152 (1989)). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832 (1991), Ladner et al., U.S. Pat. No. 5,223,409, Huse, international publication No. WO 92/06204, and region-directed mutagenesis (Derbyshire et al., *Gene* 46:145 (1986), and Ner et al., *DNA* 7:127, (1988)).

Variants of the disclosed zCTGF4 nucleotide and polypeptide sequences can also be generated through DNA shuffling as disclosed by Stemmer, *Nature* 370:389 (1994), Stemmer, *Proc. Nat'l Acad. Sci. USA* 91:10747 (1994), and international publication No. WO 97/20078. Briefly, variant DNA molecules are generated by in vitro homologous recombination by random fragmentation of a parent DNA followed by reassembly using PCR, resulting in randomly introduced point mutations. This technique can be modified by using a family of parent DNA molecules, such as allelic variants or DNA molecules from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode biologically active polypeptides, or polypeptides that bind with anti-zCTGF4 antibodies, can be recovered from the host cells and rapidly sequenced using modern equipment. These methods allow the rapid determination of the importance of individual amino acid residues in a polypeptide of interest, and can be applied to polypeptides of unknown structure.

Essential amino acids in the polypeptides of the present invention can be identified according to procedures known in the art, such as site-directed mutagenesis or alanine-scanning mutagenesis (Cunningham and Wells, *Science* 244:1081 (1989), Bass et al., *Proc. Nat'l Acad. Sci. USA* 88:4498 (1991), Coombs and Corey, "Site-Directed Mutagenesis and Protein Engineering," in *Proteins: Analysis and Design,* Angeletti (ed.), pages 259–311 (Academic Press, Inc. 1998)). In the latter technique, single alanine mutations are introduced at every residue in the molecule, and the resultant mutant molecules are tested for biological activity as disclosed below to identify amino acid residues that are critical to the activity of the molecule. See also, Hilton et al., *J. Biol. Chem.* 271:4699 (1996). The identities of essential amino acids can also be inferred from analysis of homologies with zCTGF4.

The location of zCTGF4 receptor binding domains can be identified by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306 (1992), Smith et al., *J. Mol. Biol.* 224:899 (1992), and Wlodaver et al., FEBS Lett. 309:59 (1992). Moreover, zCTGF4 labeled with biotin or FITC can be used for expression cloning of zCTGF4 receptors.

The present invention also includes "functional fragments" of zCTGF4 polypeptides and nucleic acid molecules encoding such functional fragments. As previously described herein, zCTGF4 is characterized by a multidomain structure comprising a IBP domain (amino acid residue 59 (Pro) to 102 (Tyr) of SEQ ID NO: 2) that has been suggested as an insulin growth factor binding domain, a von Willebrand factor c domain (amino acid residue 114 (Cys) to 179 (Cys) of SEQ ID NO: 2), a variable domain (amino acid 180 (Ser) to 208 (Lys), and a sulfated glycoconjugate binding motif domain (amino acid residue 209 (Cys) to 252 (Cys) of SEQ ID NO: 2). Thus, the present invention further provides fusion proteins encompassing (a) polypeptide molecules comprising one or more of the domains described above, and (b) biologically active fragments comprising portions of one or more of the domains. The other polypeptide may be another domains from another CTGF, a non-native and/or an unrelated secretory signal peptide to facilitate secretion of the fusion protein.

Routine deletion analyses of nucleic acid molecules can be performed to obtain functional fragments of a nucleic acid molecule that encodes an zCTGF4 polypeptide. As an illustration, DNA molecules having the nucleotide sequence of SEQ ID NO:1 can be digested with Bal31 nuclease to obtain a series of nested deletions. The fragments are then inserted into expression vectors in proper reading frame, and the expressed polypeptides are isolated and tested for zCTGF4, or for the ability to bind anti-zCTGF4 antibodies. One alternative to exonuclease digestion is to use oligonucleotide-directed mutagenesis to introduce deletions or stop codons to specify production of a desired fragment. Alternatively, particular fragments of an zCTGF4 gene can be synthesized using the polymerase chain reaction.

Standard methods for identifying functional domains are well-known to those of skill in the art. For example, studies on the truncation at either or both termini of interferons have been summarized by Horisberger and Di Marco, *Pharmac. Ther.* 66:507 (1995). Moreover, standard techniques for functional analysis of proteins are described by, for example, Treuter et al., *Molec. Gen. Genet.* 240:113 (1993), Content et al., "Expression and preliminary deletion analysis of the 42 kDa 2–5A synthetase induced by human interferon," in Biological Interferon Systems, *Proceedings of ISIR-TNO Meeting on Interferon Systems,* Cantell (ed.), pages 65–72 (Nijhoff 1987), Herschman, "The EGF Receptor," in *Control of Animal Cell Proliferation, Vol.* 1, Boynton et al., (eds.) pages 169–199 (Academic Press 1985), Coumailleau et al., *J. Biol. Chem.* 270:29270 (1995); Fukunaga et al., *J. Biol. Chem.* 270:25291 (1995); Yamaguchi et al., *Biochem. Pharmacol.* 50:1295 (1995), and Meisel et al., *Plant Molec. Biol.* 30:1 (1996).

The present invention also contemplates functional fragments of an zCTGF4 gene that has amino acid changes, compared with the amino acid sequence of SEQ ID NO:2. A variant zCTGF4 gene can be identified on the basis of structure by determining the level of identity with nucleotide and amino acid sequences of SEQ ID NOs:1 and 2, as discussed above. An alternative approach to identifying a variant gene on the basis of structure is to determine whether a nucleic acid molecule encoding a potential variant zCTGF4 gene can hybridize to a nucleic acid molecule having the nucleotide sequence of SEQ ID NO:1, as discussed above.

The present invention also provides polypeptide fragments or peptides comprising an epitope-bearing portion of an zCTGF4 polypeptide described herein. Such fragments or peptides may comprise an "immunogenic epitope," which is a part of a protein that elicits an antibody response when the entire protein is used as an immunogen. Immunogenic epitope-bearing peptides can be identified using standard methods (see, for example, Geysen et al., *Proc. Nat'l Acad. Sci. USA* 81:3998 (1983)).

In contrast, polypeptide fragments or peptides may comprise an "antigenic epitope," which is a region of a protein molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a protein can be used to stimulate the production of antibodies against the protein (see, for example, Sutcliffe et al., *Science* 219:660 (1983)). Accordingly, antigenic epitope-bearing peptides and polypeptides of the present invention are useful to raise antibodies that bind with the polypeptides described herein.

Antigenic epitope-bearing peptides and polypeptides preferably contain at least four to ten amino acids, at least ten to fifteen amino acids, or about 15 to about 30 amino acids of SEQ ID NO:2. Such epitope-bearing peptides and polypeptides can be produced by fragmenting an zCTGF4 polypeptide, or by chemical peptide synthesis, as described herein. Moreover, epitopes can be selected by phage display of random peptide libraries (see, for example, Lane and Stephen, *Curr. Opin. Immunol.* 5:268 (1993), and Cortese et al., *Curr. Opin. Biotechnol.* 7:616 (1996)). Standard methods for identifying epitopes and producing antibodies from small peptides that comprise an epitope are described, for example, by Mole, "Epitope Mapping," in *Methods in Molecular Biology, Vol.* 10, Manson (ed.), pages 105–116 (The Humana Press, Inc. 1992), Price, "Production and Characterization of Synthetic Peptide-Derived Antibodies," in *Monoclonal Antibodies: Production, Engineering, and Clinical Application,* Ritter and Ladyman (eds.), pages 60–84 (Cambridge University Press 1995), and Coligan et al. (eds.), *Current Protocols in Immunology,* pages 9.3.1–9.3.5 and pages 9.4.1–9.4.11 (John Wiley & Sons 1997).

Regardless of the particular nucleotide sequence of a variant zCTGF4 gene, the gene encodes a polypeptide that is characterized by its proliferative or differentiating activity, or ability to induce specialized cell functions, or by the ability to bind specifically to an anti-zCTGF4 antibody. More specifically, variant zCTGF4 genes encode polypeptides which exhibit at least 50% and preferably, greater than 70, 80 or 90%, of the activity of polypeptide encoded by the human zCTGF4 gene described herein.

For any zCTGF4 polypeptide, including variants and fusion proteins, one of ordinary skill in the art can readily generate a fully degenerate polynucleotide sequence encoding that variant using the information set forth in Tables 1 and 2 above.

The present invention further provides a variety of other polypeptide fusions (and related multimeric proteins comprising one or more polypeptide fusions). For example, a zCTGF4 polypeptide can be prepared as a fusion to a dimerizing protein as disclosed in U.S. Pat. Nos. 5,155,027 and 5,567,584. Preferred dimerizing proteins in this regard include immunoglobulin constant region domains. Immunoglobulin-zCTGF4 polypeptide fusions can be expressed in genetically engineered cells (to produce a variety of multimeric zCTGF4 analogs). Auxiliary domains can be fused to zCTGF4 polypeptides to target them to specific cells, tissues, or macromolecules (e.g., collagen). For example, a zCTGF4 polypeptide or protein could be targeted to a predetermined cell type by fusing a zCTGF4 polypeptide to a ligand that specifically binds to a receptor on the surface of the target cell. In this way, polypeptides and proteins can be targeted for therapeutic or diagnostic purposes. A zCTGF4 polypeptide can be fused to two or more moieties, such as an affinity tag for purification and a targeting domain. Polypeptide fusions can also comprise one or more cleavage sites, particularly between domains. See, Tuan et al., *Connective Tissue Research* 34:1–9, 1996.

A Hopp/Woods hydrophilicity profile of the zCTGF4 protein sequence as shown in SEQ ID NO:2 can be generated (Hopp et al., *Proc. Natl. Acad. Sci.* 78:3824–3828, 1981; Hopp, *J. Immun. Meth.* 88:1–18, 1986 and Triquier et al., *Protein Engineering* 11:153–169, 1998). The profile is based on a sliding six-residue window. Buried G, S, and T residues and exposed H, Y, and W residues were ignored. Hydrophilicity can be used to determine regions that have the most antigenic potential. For example, in zCTGF4, hydrophilic regions include amino acid residues 239–244 of SEQ ID NO: 2, amino acid residues 105–110 of SEQ ID NO: 2, amino acid residues 172–177 of SEQ ID NO: 2, amino acid residues 238–243 of SEQ ID NO: 2, and amino acid residues 171–176 of SEQ ID NO: 2.

Using the methods discussed herein, one of ordinary skill in the art can identify and/or prepare a variety of polypeptides that are have substantially similar sequence identity to residues 1 or 24 to 354 of SEQ ID NO: 2, or functional fragments and fusions thereof, and retain the properties of the wild-type protein such as the ability to stimulate proliferation, differentiation or induce specialized cell function.

The polypeptides of the present invention, including full-length proteins, fragments thereof and fusion proteins, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., Molecular Cloning: A *Laboratory Manual*, 2nd ed., Cold Spring Harbor Laboratory Press, Cold Spring Harbor, N.Y., 1989, and Ausubel et al., eds., *Current Protocols in Molecular Biology*, John Wiley and Sons, Inc., NY, 1987.

In general, a DNA sequence encoding a zCTGF4 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a zCTGF4 polypeptide into the secretory pathway of a host cell, a secretory signal sequence (also known as a leader sequence, prepro sequence or pre sequence) is provided in the expression vector. The secretory signal sequence may be that of the zCTGF4 polypeptide, or may be derived from another secreted protein (e.g., t-PA) or synthesized de novo. The secretory signal sequence is operably linked to the zCTGF4 DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain secretory signal sequences may be positioned elsewhere in the DNA sequence of interest (see, e.g., Welch et al., U.S. Pat. No. 5,037,743; Holland et al., U.S. Pat. No. 5,143,830).

Alternatively, the secretory signal sequence contained in the polypeptides of the present invention is used to direct other polypeptides into the secretory pathway. The present invention provides for such fusion polypeptides. A signal fusion polypeptide can be made wherein a secretory signal sequence derived from amino acid residue 1 to 23 of SEQ ID NO:2 is operably linked to a DNA sequence encoding another polypeptide using methods known in the art and disclosed herein. The secretory signal sequence contained in the fusion polypeptides of the present invention is preferably fused amino-terminally to an additional peptide to direct the additional peptide into the secretory pathway. Such constructs have numerous applications known in the art. For example, these novel secretory signal sequence fusion constructs can direct the secretion of an active component of a normally non-secreted protein. Such fusions may be used in vivo or in vitro to direct peptides through the secretory pathway.

Cultured mammalian cells are suitable hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–845, 1982), DEAE-dextran mediated transfection (Ausubel et al., *ibid.*), and liposome-mediated transfection (Hawley-Nelson et al., *Focus* 15:73, 1993; Ciccarone et al., *Focus* 15:80, 1993), and viral vectors (Miller and Rosman, *BioTechniques* 7:980–90, 1989; Wang and Finer, *Nature Med.* 2:714–6, 1996). The production of recombinant polypeptides in cultured mammalian cells is disclosed, for example, by Levinson et al., U.S. Pat. No. 4,713,339; Hagen et al., U.S. Pat. No. 4,784, 950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59–72, 1977) and Chinese hamster ovary (e.g. CHO-K1; ATCC No. CCL 61) cell lines. Additional suitable cell lines are known in the art and available from public depositories such as the American Type Culture Collection, Manassas, Va. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601, 978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate.

Other drug resistance genes (e.g. hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Other higher eukaryotic cells can also be used 10 as hosts, including plant cells, insect cells and avian cells. The use of *Agrobacterium rhizogenes* as a vector for expressing genes in plant cells has been reviewed by Sinkar et al., *J. Biosci. (Bangalore)* 11:47–58, 1987. Transformation of insect cells and production of foreign polypeptides therein is disclosed by Guarino et al., U.S. Pat. No. 5,162,222 and WIPO publication WO 94/06463. Insect cells can be infected with recombinant baculovirus, commonly derived from *Autographa californica* nuclear polyhedrosis virus (AcNPV). DNA encoding the zCTGF4 polypeptide is inserted into the baculoviral genome in place of the AcNPV polyhedrin gene coding sequence by one of two methods. The first is the traditional method of homologous DNA recombination between wild-type AcNPV and a transfer vector containing the zCTGF4 flanked by AcNPV sequences. Suitable insect cells, e.g. SF9 cells, are infected with wild-type AcNPV and transfected with a transfer vector comprising a zCTGF4 polynucleotide operably linked to an AcNPV polyhedrin gene promoter, terminator, and flanking sequences. See, King, L. A. and Possee, R. D., *The Baculovirus Expression System: A Laboratory Guide,* London, Chapman & Hall; O'Reilly, D. R. et al., *Baculovirus Expression Vectors: A Laboratory Manual,* New York, Oxford University Press., 1994; and, Richardson, C. D., Ed., *Baculovirus Expression Protocols. Methods in Molecular Biology,* Totowa, N. J., Humana Press, 1995. Natural recombination within an insect cell will result in a recombinant baculovirus which contains zCTGF4 driven by the polyhedrin promoter. Recombinant viral stocks are made by methods commonly used in the art.

The second method of making recombinant baculovirus utilizes a transposon-based system described by Luckow (Luckow, V. A, et al., *J Virol* 67:4566–79, 1993). This system is sold in the Bac-to-Bac kit (Life Technologies, Rockville, Md.). This system utilizes a transfer vector, pFastBac1™ (Life Technologies) containing a Tn7 transposon to move the DNA encoding the zCTGF4 polypeptide into a baculovirus genome maintained in *E. coli* as a large plasmid called a "bacmid." The pFastBac1™ transfer vector utilizes the AcNPV polyhedrin promoter to drive the expression of the gene of interest, in this case zCTGF4. However, pFastBac1™ can be modified to a considerable degree. The polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins. See, Hill-Perkins, M. S. and Possee, R. D., *J. Gen. Virol.* 71:971–6, 1990; Bonning, B. C. et al., *J. Gen. Virol.* 75:1551–6, 1994; and, Chazenbalk, G. D., and Rapoport, B., *J. Biol. Chem.* 270:1543–9, 1995. In such transfer vector constructs, a short or long version of the basic protein promoter can be used. Moreover, transfer vectors can be constructed which replace the native zCTGF4 secretory signal sequences with secretory signal sequences derived from insect proteins. For example, a secretory signal sequence from Ecdysteroid Glucosyltransferase (EGT), honey bee Melittin (Invitrogen, Carlsbad, Calif.), or baculovirus gp67 (PharMingen, San Diego, Calif.) can be used in constructs to replace the native zCTGF4 secretory signal sequence. In addition, transfer vectors can include an in-frame fusion with DNA encoding an epitope tag at the C- or N-terminus of the expressed zCTGF4 polypeptide, for example, a Glu-Glu epitope tag (Grussenmeyer, T. et al., *Proc. Natl. Acad. Sci.* 82:7952–4, 1985). Using a technique known in the art, a transfer vector containing zCTGF4 is transformed into *E. Coli,* and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses zCTGF4 is subsequently produced. Recombinant viral stocks are made by methods commonly used the art.

The recombinant virus is used to infect host cells, typically a cell line derived from the fall armyworm, *Spodoptera frugiperda.* See, in general, Glick and Pasternak, *Molecular Biotechnology: Principles and Applications of Recombinant DNA,* ASM Press, Washington, D.C., 1994. Another suitable cell line is the High FiveO™ cell line (Invitrogen) derived from *Trichoplusia ni* (U.S. Pat. No. 5,300,435). Commercially available serum-free media are used to grow and maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. The cells are grown up from an inoculation density of approximately 2–5×$10^5$ cells to a density of 1–2×$10^6$ cells at which time a recombinant viral stock is added at a multiplicity of infection (MOI) of 0.1 to 10, more typically near 3. The recombinant virus-infected cells typically produce the recombinant zCTGF4 polypeptide at 12–72 hours post-infection and secrete it with varying efficiency into the medium. The culture is usually harvested 48 hours post-infection. Centrifugation is used to separate the cells from the medium (supernatant). The supernatant containing the zCTGF4 polypeptide is filtered through micropore filters, usually 0.45 $\mu$m pore size. Procedures used are generally described in available laboratory manuals (King, L. A. and Possee, R. D., ibid.; O'Reilly, D. R. et al., ibid.; Richardson, C. D., ibid.). Subsequent purification of the zCTGF4 polypeptide from the supernatant can be achieved using methods described herein.

Fungal cells, including yeast cells, can also be used within the present invention. Yeast species of particular interest in this regard include *Saccharomyces cerevisiae, Pichia pastoris,* and *Pichia methanolica.* Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No.

4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459–65, 1986 and Cregg, U.S. Pat. No. 4,882,279. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

The use of *Pichia methanolica* as host for the production of recombinant proteins is disclosed in WIPO Publications WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant ($\tau$) of from 1 to 40 milliseconds, most preferably about 20 milliseconds.

Prokaryotic host cells, including strains of the bacteria *Escherichia coli*, Bacillus and other genera are also useful host cells within the present invention. Techniques for transforming these hosts and expressing foreign DNA sequences cloned therein are well known in the art (see, e.g., Sambrook et al., ibid.). When expressing a zCTGF4 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

Expressed recombinant zCTGF4 polypeptides (or chimeric zCTGF4 polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa,), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. See, for example, *Affinity Chromatography: Principles & Methods*, Pharmacia LKB Biotechnology, Uppsala, Sweden, 1988.

The polypeptides of the present invention can be isolated by exploitation of size, charge and hydrophobicity. For example, immobilized metal ion adsorption (IMAC) chromatography can be used to purify histidine-rich proteins (E. Sulkowski, *Trends in Biochem.* 3:1–7, 1985). Other methods of purification include purification of glycosylated proteins by lectin affinity chromatography and ion exchange chromatography (*Methods in Enzymol.*, Vol. 182, "Guide to Protein Purification", M. Deutscher, (ed.), Acad. Press, San Diego, 1990, pp.529–39). Within additional embodiments of the invention, a fusion of the polypeptide of interest and an affinity tag (e.g., maltose-binding protein, an immunoglobulin domain) may be constructed to facilitate purification. ZCTGF4 has a domain homologous to the heparin binding domain described previously for CTGF, and exploitation of this property may be useful for purification of zCTGF4. For a review, see, Burgess et al., *Ann. Rev. of Biochem.* 58:575–606, 1989. Members of the FGF family, which also have a heparin binding domain can be purified to apparent homogeneity by heparin-Sepharose affinity chromatography (Gospodarowicz et al., *Proc. Natl. Acad. Sci.* 81:6963–6967, 1984) and eluted using linear step gradients of NaCl (Ron et al., *J. Biol. Chem.* 268(4):2984–2988, 1993; *Chromatography: Principles & Methods*, pp. 77–80, Pharmacia LKB Biotechnology, Uppsala, Sweden, 1993; in "Immobilized Affinity Ligand Techniques", Hermanson et al., eds., pp. 165–167, Academic Press, San Diego, 1992; Kjellen et al., *Ann. Rev. Biochem.Ann. Rev. Biochem.* 60:443–474, 1991; and Ke et al., *Protein Expr. Purif.* 3(6):497–507, 1992.)

Protein refolding (and optionally reoxidation) procedures may be advantageously used. It is preferred to purify the protein to >80% purity, more preferably to >90% purity, even more preferably >95%, and particularly preferred is a pharmaceutically pure state, that is greater than 99.9% pure with respect to contaminating macromolecules, particularly other proteins and nucleic acids, and free of infectious and pyrogenic agents. Preferably, a purified protein is substantially free of other proteins, particularly other proteins of animal origin.

ZCTGF4 polypeptides or fragments thereof may also be prepared through chemical synthesis (Merrifield, *J. Am. Chem. Soc.* 85:2149, 1963). ZCTGF4 polypeptides may be monomers or multimers; glycosylated or non-glycosylated; pegylated or non-pegylated; and may or may not include an initial methionine amino acid residue.

The activity of molecules of the present invention can be measured using a variety of assays that measure cell proliferation, differentiation, chemotaxis or induction of specialized cell functions. Of particular interest are changes in proliferation or differentiation of endothelial cells, particularly endothelial cells isolated from testis, trachea, bone marrow or kidney tissue. Proliferation and differentiation can be measured using in vitro using cultured cells or in vivo by administering molecules of the claimed invention to the appropriate animal model. Assays measuring cell proliferation or differentiation are well known in the art. For example, assays measuring proliferation include such assays as chemosensitivity to neutral red dye (Cavanaugh et al., *Investigational New Drugs* 8:347–354, 1990, incorporated herein by reference), incorporation of radiolabelled nucleotides (Cook et al., *Analytical Biochem.* 179:1–7, 1989, incorporated herein by reference), incorporation of 5-bromo-2'-deoxyuridine (BrdU) in the DNA of proliferating cells (Porstmann et al., *J. Immunol. Methods* 82:169–179, 1985, incorporated herein by reference), and use of tetrazolium salts (Mosmann, *J. Immunol. Methods* 65:55–63, 1983; Alley et al., *Cancer Res.* 48:589–601, 1988; Marshall et al., *Growth Reg.* 5:69–84, 1995; and Scudiero et al., *Cancer Res.* 48:4827–4833, 1988; all incorporated herein by reference). Assays measuring differentiation include, for example, measuring cell-surface markers associated with stage-specific expression of a tissue, enzymatic activity, functional activity or morphological changes (Watt, *FASEB*, 5:281–284, 1991; Francis, *Differentiation* 57:63–75, 1994; Raes, *Adv. Anim. Cell Biol. Technol. Bioprocesses*, 161–171, 1989; all incorporated herein by reference).

Examples of assays measuring induction of specialized cell functions include: extracellular matrix protein mRNA induction assays (Frazier et al., *J. Invest. Dermatol.* 107:404–411, 1996); $^{35}$S methionine pulse-chase assays measuring stimulation of matrix protein synthesis (Frazier et al., ibid., 1996); subcutaneous administration of growth factors to mice (Roberts et al., *Proc. Natl. Acad. Sci. USA* 83:4167–4171, 1986); and in situ hybridization to measure changes in mRNA expression (Fava et al., *Blood* 76:1946–1955, 1990).

An exemplary in vivo assay is when mammalian transfected (or co-transfected) expression host cells may be embedded in an alginate environment and injected (implanted) into recipient animals. Alginate-poly-L-lysine microencapsulation, permselective membrane encapsulation and diffusion chambers have been described as a means to entrap transfected mammalian cells or primary mammalian cells. These types of non-immunogenic "encapsulations" or microenvironments permit the transfer of nutrients into the microenvironment, and also permit the diffusion of proteins and other macromolecules secreted or released by the captured cells across the environmental barrier to the recipient animal. Most importantly, the capsules or microenvironments mask and shield the foreign, embedded cells from the recipient animal's immune response. Such microenvironments can extend the life of the injected cells from a few hours or days (naked cells) to several weeks (embedded cells).

An in vivo approach for assaying proteins of the present invention involves viral delivery systems. Exemplary viruses for this purpose include adenovirus, herpesvirus, retroviruses, vaccinia virus, and adeno-associated virus (AAV). Adenovirus, a double-stranded DNA virus, is currently the best studied gene transfer vector for delivery of heterologous nucleic acid (for review, see Becker et al., *Meth. Cell Biol.* 43:161–89, 1994; and Douglas and Curiel, *Science & Medicine* 4:44–53, 1997). The adenovirus system offers several advantages: (i) adenovirus can accommodate relatively large DNA inserts; (ii) can be grown to high-titer; (iii) infect a broad range of mammalian cell types; and (iv) can be used with many different promoters including ubiquitous, tissue specific, and regulatable promoters. Also, because adenoviruses are stable in the bloodstream, they can be administered by intravenous injection.

Using adenovirus vectors where portions of the adenovirus genome are deleted, inserts are incorporated into the viral DNA by direct ligation or by homologous recombination with a co-transfected plasmid. In an exemplary system, the essential E1 gene has been deleted from the viral vector, and the virus will not replicate unless the E1 gene is provided by the host cell (the human 293 cell line is exemplary). When intravenously administered to intact animals, adenovirus primarily targets the liver. If the adenoviral delivery system has an E1 gene deletion, the virus cannot replicate in the host cells. However, the host's tissue (e.g., liver) will express and process (and, if a secretory signal sequence is present, secrete) the heterologous protein. Secreted proteins will enter the circulation in the highly vascularized liver, and effects on the infected animal can be determined.

Moreover, adenoviral vectors containing various deletions of viral genes can be used in an attempt to reduce or eliminate immune responses to the vector. Such adenoviruses are E1 deleted, and in addition contain deletions of E2A or E4 (Lusky, M. et al., *J. Virol.* 72:2022–2032, 1998;

Raper, S. E. et al., *Human Gene Therapy* 9:671–679, 1998). In addition, deletion of E2b is reported to reduce immune responses (Amalfitano, A. et al., *J. Virol.* 72:926–933, 1998). Moreover, by deleting the entire adenovirus genome, very large inserts of heterologous DNA can be accommodated. Generation of so called "gutless" adenoviruses where all viral genes are deleted are particularly advantageous for insertion of large inserts of heterologous DNA. For review, see Yeh, P. and Perricaudet, M., *FASEB J.* 11:615–623, 1997.

The adenovirus system can also be used for protein production in vitro. By culturing adenovirus-infected non-293 cells under conditions where the cells are not rapidly dividing, the cells can produce proteins for extended periods of time. For instance, BHK cells are grown to confluence in cell factories, then exposed to the adenoviral vector encoding the secreted protein of interest. The cells are then grown under serum-free conditions, which allows infected cells to survive for several weeks without significant cell division. Alternatively, adenovirus vector infected 293 cells can be grown as adherent cells or in suspension culture at relatively high cell density to produce significant amounts of protein (See Garnier et al., *Cytotechnol* 15:145–155, 1994). With either protocol, an expressed, secreted heterologous protein can be repeatedly isolated from the cell culture supernatant, lysate, or membrane fractions depending on the disposition of the expressed protein in the cell. Within the infected 293 cell production protocol, non-secreted proteins may also be effectively obtained.

Assays can be used to measure other cellular responses, that include, chemotaxis, adhesion, changes in ion channel influx, regulation of second messenger levels and neurotransmitter release. Such assays are well known in the art. See, for example, in "Basic & Clinical Endocrinology Ser., Vol. Vol. 3," *Cytochemical Bioassays: Techniques & Applications,* Chayen; Chayen, Bitensky, eds., Dekker, N.Y., 1983.

In view of the tissue distribution observed for this zCTGF4, agonists (including the natural ligand) and antagonists have enormous potential in both in vitro and in vivo applications. Compounds identified as zCTGF4 agonists are useful for stimulating proliferation and/or differentiation of cells in culture. For example, agonist compounds are useful as components of defined cell culture media, and may be used alone or in combination with other cytokines and hormones to replace serum that is commonly used in cell culture. Agonists are thus useful in specifically promoting the growth and/or development of cells derived from testis, trachea, bone marrow or kidney tissues or endothelial and ligament-derived fibroblast cells in culture.

Agonists (including zCTGF4) will be useful for increasing production of extracellular matrix components, and may be used in the treatment of connective tissue. Particularly, agonists will be useful as treatment for ligaments, cartilage and tendons. By virtue of the tissue distribution for the expression of these molecules, agonists will be useful for enhancing healing and stabilizing wounds and as a component artificial skin. The presence of zCTGF4 expression in the bone marrow suggests that the molecules of the present invention play a role in hematopoiesis. That role is likely indirect, where stromal cells within the architecture of the bone marrow secrete zCTGF4, modulating production of cells of the hematopoietic lineage.

Antagonists will be useful for inhibiting expression of specialized cell functions, such as production of extracellular components and inhibition of cell proliferation. Genes encoding polypeptides having potential zCTGF4 polypeptide binding domains can be obtained by screening random peptide libraries displayed on phage (phage display) or on bacteria, such as *E. coli.* Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the zCTGF4 sequences disclosed herein to identify proteins which bind to zCTGF4. These "binding proteins" which interact with ZCTGF4 polypeptides may be used for tagging cells; for isolating homolog polypeptides by affinity purification; they can be directly or indirectly conjugated to drugs, toxins, radionuclides and the like. These binding proteins can also be used in analytical methods such as for screening expression libraries and neutralizing activity. The binding proteins can also be used for diagnostic assays for determining circulating levels of polypeptides; for detecting or quantitating soluble polypeptides as marker of underlying pathology or disease. These binding proteins can also act as zCTGF4 "antagonists" to block zCTGF4 binding and signal transduction in vitro and in vivo. These anti- zCTGF4 binding proteins would be useful for inhibiting expression of genes which result in proliferation, differentiation or induction of specialized cell functions, such as production of excellular matrix. Such anti-zCTGF4 binding proteins can be used for treatment in bone marrow fibrosis, modulating production or differentiation of hematopoietic cells, prevention of scar tissue formation, cutaneous lupus erythematosis, scleroderma, dermatositis, and end-stage kidney failure, alone or combination with other therapies.

zCTGF4 can also be used to identify inhibitors (antagonists) of its activity. Test compounds are added to the assays disclosed herein to identify compounds that inhibit the activity of zCTGF4. In addition to those assays disclosed herein, samples can be tested for inhibition of zCTGF4 activity within a variety of assays designed to measure receptor binding or the stimulation/inhibition of zCTGF4-dependent cellular responses. For example, zCTGF4-responsive cell lines can be transfected with a reporter gene construct that is responsive to a zCTGF4-stimulated cellular pathway. Reporter gene constructs of this type are known in the art, and will generally comprise a zCTGF4-DNA response element operably linked to a gene encoding an assayable protein, such as luciferase. DNA response elements can include, but are not limited to, cyclic AMP response elements (CRE), hormone response elements (HRE) insulin response element (IRE) (Nasrin et al., *Proc. Natl. Acad. Sci. USA* 87:5273–7, 1990) and serum response elements (SRE) (Shaw et al. *Cell* 56: 563–72, 1989). Cyclic AMP response elements are reviewed in Roestler et al., *J. Biol. Chem.* 263 (19) :9063–6; 1988 and Habener, *Molec. Endocrinol.* 4 (8):1087–94; 1990. Hormone response elements are reviewed in Beato, *Cell* 56:335–44; 1989. Candidate compounds, solutions, mixtures or extracts are tested for the ability to inhibit the activity of zCTGF4 on the target cells as evidenced by a decrease in zCTGF4 stimulation of reporter gene expression. Assays of this type will detect compounds that directly block zCTGF4 binding to cell-surface receptors, as well as compounds that block processes in the cellular pathway subsequent to receptor-ligand binding. In the alternative, compounds or other samples can be tested for direct blocking of zCTGF4 binding to receptor using zCTGF4 tagged with a detectable label (e.g., $^{125}$I, biotin, horseradish peroxidase, FITC, and the like). Within assays of this type, the ability of a test sample to inhibit the binding of labeled zCTGF4 to the receptor is indicative of inhibitory activity, which can be confirmed through secondary assays. Receptors used within binding assays may be cellular receptors or isolated, immobilized receptors.

A ZCTGF4 polypeptide can be expressed as a fusion with an immunoglobulin heavy chain constant region, typically an $F_c$ fragment, which contains two constant region domains and lacks the variable region. Methods for preparing such fusions are disclosed in U.S. Pat. Nos. 5,155,027 and 5,567,584. Such fusions are typically secreted as multimeric molecules wherein the Fc portions are disulfide bonded to each other and two non-Ig polypeptides are arrayed in closed proximity to each other. Fusions of this type can be used to affinity purify ligand, as an in vitro assay tool, or antagonist. For use in assays, the chimeras are bound to a support via the Fc region and used in an ELISA format.

A zCTGF4 ligand-binding polypeptide can also be used for purification of ligand. The polypeptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting medium will generally be configured in the form of a column, and fluids containing ligand are passed through the column one or more times to allow ligand to bind to the receptor polypeptide. The ligand is then eluted using changes in salt concentration, chaotropic agents (guanidine HC1), or pH to disrupt ligand-receptor binding.

An assay system that uses a ligand-binding receptor (or an antibody, one member of a complement/anti-complement pair) or a binding fragment thereof, and a commercially available biosensor instrument (BIAcore, Pharmacia Biosensor, Piscataway, N.J.) may be advantageously employed. Such receptor, antibody, member of a complement/anti-complement pair or fragment is immobilized onto the surface of a receptor chip. Use of this instrument is disclosed by Karlsson, *J. Immunol. Methods* 145:229–40, 1991 and Cunningham and Wells, *J. Mol. Biol.* 234:554–63, 1993. A receptor, antibody, member or fragment is covalently attached, using amine or sulfhydryl chemistry, to dextran fibers that are attached to gold film within the flow cell. A test sample is passed through the cell. If a ligand, epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding.

Ligand-binding receptor polypeptides can also be used within other assay systems known in the art. Such systems include Scatchard analysis for determination of binding affinity (see Scatchard, *Ann. NY Acad. Sci.* 51: 660–72, 1949) and calorimetric assays (Cunningham et al., *Science* 253:545–48, 1991; Cunningham et al., *Science* 245:821–25, 1991).

ZCTGF4 polypeptides can also be used to prepare antibodies that bind to zCTGF4 epitopes, peptides or polypeptides. The zCTGF4 polypeptide or a fragment thereof serves as an antigen (immunogen) to inoculate an animal and elicit an immune response. One of skill in the art would recognize that antigenic, epitope-bearing polypeptides contain a sequence of at least 6, preferably at least 9, and more preferably at least 15 to about 30 contiguous amino acid residues of a zCTGF4 polypeptide (e.g., SEQ ID NO:2). Polypeptides comprising a larger portion of a zCTGF4 polypeptide, i.e., from 30 to 10 residues up to the entire length of the amino acid sequence are included. Antigens or immunogenic epitopes can also include attached tags, adjuvants and carriers, as described herein. Suitable antigens include the zCTGF4 polypeptide encoded by SEQ ID NO:2 from amino acid number 24 to amino acid number 354, or a contiguous 9 to 330 amino acid fragment thereof. Other suitable antigens include the IBP domain (residues 59–102), von Willebrand factor c domain (residues 114–179), variable domain (residues 180–208), and sulfated glyconconjugate binding motif domain (residues 209–252) as disclosed herein. Preferred peptides to use as antigens are hydrophilic peptides such as those predicted by one of skill in the art from a hydrophobicity plot (See Figure). ZCTGF4 hydrophilic peptides include peptides comprising amino acid sequences selected from the group consisting of: residues 239–244, residues 105–110, residues 172–177, residues 238–243 and residues 171–176, all of SEQ ID NO:2. Antibodies from an immune response generated by inoculation of an animal with these antigens can be isolated and purified as described herein. Methods for preparing and isolating polyclonal and monoclonal antibodies are well known in the art. See, for example, *Current Protocols in Immunology,* Cooligan, et al. (eds.), National Institutes of Health, John Wiley and Sons, Inc., 1995; Sambrook et al., *Molecular Cloning: A Laboratory Manual, Second Edition,* Cold Spring Harbor, N.Y., 1989; and Hurrell, J. G. R., Ed., *Monoclonal Hybridoma Antibodies: Techniques and Applications,* CRC Press, Inc., Boca Raton, Fla., 1982.

As would be evident to one of ordinary skill in the art, polyclonal antibodies can be generated from inoculating a variety of warm-blooded animals such as horses, cows, goats, sheep, dogs, chickens, rabbits, mice, and rats with a zCTGF4 polypeptide or a fragment thereof.

The immunogenicity of a zCTGF4 polypeptide may be increased through the use of an adjuvant, such as alum (aluminum hydroxide) or Freund's complete or incomplete adjuvant. Polypeptides useful for immunization also include fusion polypeptides, such as fusions of zCTGF4 or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as $F(ab')_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Moreover, human antibodies can be produced in transgenic, non-human animals that have been engineered to contain human immunoglobulin genes as disclosed in WIPO Publication WO 98/24893. It is preferred that the endogenous immunoglobulin genes in these animals be inactivated or eliminated, such as by homologous recombination.

Antibodies are considered to be specifically binding if: 1) they exhibit a threshold level of binding activity, and 2) they do not significantly cross-react with related polypeptide molecules. A threshold level of binding is determined if anti-zCTGF4 antibodies herein bind to a zCTGF4 polypeptide, peptide or epitope with an affinity at least 10-fold greater than the binding affinity to control (non-zCTGF4) polypeptide. It is preferred that the antibodies exhibit a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, G., Ann. NY Acad. Sci. 51: 660–672, 1949).

Whether anti-zCTGF4 antibodies do not significantly cross-react with related polypeptide molecules is shown, for example, by the antibody detecting zCTGF4 polypeptide but not known related polypeptides using a standard Western blot analysis (Ausubel et al., ibid.). Examples of known related polypeptides are those disclosed in the prior art, such as known orthologs, and paralogs, and similar known members of a protein family, such as other known human CTGFs (e.g., CTGF and CTGF-2). Screening can also be done using non-human zCTGF4, and zCTGF4 mutant polypeptides. Moreover, antibodies can be "screened against" known related polypeptides, to isolate a population that specifically binds to the zCTGF4 polypeptides. For example, antibodies raised to zCTGF4 are adsorbed to related polypeptides adhered to insoluble matrix; antibodies specific to zCTGF4 will flow through the matrix under the proper buffer conditions. Screening allows isolation of polyclonal and monoclonal antibodies non-crossreactive to known closely related polypeptides (*Antibodies: A Laboratory Manual,* Harlow and Lane (eds.), Cold Spring Harbor Laboratory Press, 1988; *Current Protocols in Immunology,* Cooligan, et al. (eds.), National Institutes of Health, John Wiley and Sons, Inc., 1995). Screening and isolation of specific antibodies is well known in the art. See, *Fundamental Immunology,* Paul (eds.), Raven Press, 1993; Getzoff et al., Adv. in Immunol. 43: 1–98, 1988; *Monoclonal Antibodies: Principles and Practice,* Goding, J. W. (eds.), *Academic Press Ltd.,* 1996; Benjamin et al., Ann. Rev. Immunol. 2: 67–101, 1984. Specifically binding anti-zCTGF4 antibodies can be detected by a number of methods in the art, and disclosed below.

A variety of assays known to those skilled in the art can be utilized to detect antibodies which bind to zCTGF4 proteins or polypeptides. Exemplary assays are described in detail in *Antibodies: A Laboratory Manual,* Harlow and Lane (Eds.), Cold Spring Harbor Laboratory Press, 1988. Representative examples of such assays include: concurrent immunoelectrophoresis, radioimmunoassay, radioimmunoprecipitation, enzyme-linked immunosorbent assay (ELISA), dot blot or Western blot assay, inhibition or competition assay, and sandwich assay. In addition, antibodies can be screened for binding to wild-type versus mutant zCTGF4 polypeptide.

Alternative techniques for generating or selecting antibodies useful herein include in vitro exposure of lymphocytes to zCTGF4 protein or peptide, and selection of antibody display libraries in phage or similar vectors (for instance, through use of immobilized or labeled zCTGF4 protein or peptide). Genes encoding polypeptides having potential zCTGF4 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the zCTGF4 sequences disclosed herein to identify proteins which bind to zCTGF4. These "binding polypeptides" which interact with zCTGF4 polypeptides can be used for tagging cells; for isolating homolog polypeptides by affinity purification; they can be directly or indirectly conjugated to drugs, toxins, radionuclides and the like. These binding polypeptides can also be used in analytical methods such as for screening expression libraries and neutralizing activity, e.g., for blocking interaction between ligand and receptor, or viral binding to a receptor. The binding polypeptides can also be used for diagnostic assays for determining circulating levels of zCTGF4 polypeptides; for detecting or quantitating soluble zCTGF4 polypeptides as marker of underlying pathology or disease. These binding polypeptides can also act as zCTGF4 "antagonists" to block zCTGF4 binding and signal transduction in vitro and in vivo. These anti-zCTGF4 binding polypeptides would be useful for inhibiting zCTGF4 activity or protein-binding.

Antibodies to zCTGF4 may be used for tagging cells that express zCTGF4; for isolating zCTGF4 by affinity purification; for diagnostic assays for determining circulating levels of zCTGF4 polypeptides; for detecting or quantitating soluble zCTGF4 as marker of underlying pathology or disease; in analytical methods employing FACS; for screening expression libraries; for generating anti-idiotypic antibodies; and as neutralizing antibodies or as antagonists to block zCTGF4 in vitro and in vivo. In particular, antibodies will be useful for diagnostics, due to the association of proteins of the present invention with extracellular matrix and vessels, and labeled proteins will be useful in the diagnosis of diseases such as bone marrow fibrosis, prevention of scar tissue formation, cutaneous lupus erythematosis, scleroderma, dermatositis, and end-stage kidney failure.

Antibodies or polypeptides herein may also be directly or indirectly conjugated to drugs, toxins, radionuclides and the like, and these conjugates used for in vivo diagnostic or therapeutic applications. Moreover, antibodies to zCTGF4 or fragments thereof may be used in vitro to detect denatured zCTGF4 or fragments thereof in assays, for example, Western Blots or other assays known in the art.

Antibodies or polypeptides herein can also be directly or indirectly conjugated to drugs, toxins, radionuclides and the like, and these conjugates used for in vivo diagnostic or therapeutic applications. For instance, polypeptides or antibodies of the present invention can be used to identify or treat tissues or organs that express a corresponding anti-complementary molecule (receptor or antigen, respectively, for instance). More specifically, zCTGF4 polypeptides or anti-zCTGF4 antibodies, or bioactive fragments or portions thereof, can be coupled to detectable or cytotoxic molecules and delivered to a mammal having cells, tissues or organs that express the anti-complementary molecule. For example, for use of the antibodies and polypeptides, labeled for detection by imaging technologies, will be useful for diagnosing diseases associated with extracellular matrix and vessels, such as, bone marrow fibrosis, aberrant hematopoiesis, prevention of scar tissue formation, cutaneous lupus erythematosis, scleroderma, dermatositis, and end-stage kidney failure.

Suitable detectable molecules may be directly or indirectly attached to the polypeptide or antibody, and include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, Pseudomonas exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the polypeptide or antibody portion. For these purposes, biotin/streptavidin is an exemplary complementary/anticomplementary pair.

In another embodiment, polypeptide-toxin fusion proteins or antibody-toxin fusion proteins can be used for targeted cell or tissue inhibition or ablation (for instance, to treat diseases caused by inappropriate growth of cells or tissues). Such molecule fusion proteins thus represent a generic targeting vehicle for cell/tissue-specific delivery of generic anti-complementary-detectable/cytotoxic molecule conjugates.

In another embodiment, zCTGF4-cytokine fusion proteins or antibody-cytokine fusion proteins can be used for enhancing in vivo killing of target tissues (for example, blood and bone marrow cancers), if the zCTGF4 polypeptide or anti-zCTGF4 antibody targets the hyperproliferative blood or bone marrow cell (See, generally, Hornick et al., *Blood* 89:4437–47, 1997). They described fusion proteins enable targeting of a cytokine to a desired site of action, thereby providing an elevated local concentration of cytokine. Suitable zCTGF4 polypeptides or anti-zCTGF4 antibodies target an undesirable cell or tissue (i.e., a tumor or a leukemia), and the fused cytokine mediated improved target cell lysis by effector cells. Suitable cytokines for this purpose include interleukin 2 and granulocyte-macrophage colony-stimulating factor (GM-CSF), for instance.

In another embodiment, if the zCTGF4 polypeptide or anti-zCTGF4 antibody targets vascular cells or tissues, such polypeptide or antibody may be conjugated with a radionuclide, and particularly with a beta-emitting radionuclide, to reduce restenosis. Such therapeutic approach poses less danger to clinicians who administer the radioactive therapy. For instance, iridium-192 impregnated ribbons placed into stented vessels of patients until the required radiation dose was delivered showed decreased tissue growth in the vessel and greater luminal diameter than the control group, which received placebo ribbons. Further, revascularisation and stent thrombosis were significantly lower in the treatment group. Similar results are predicted with targeting of a bioactive conjugate containing a radionuclide, as described herein.

The bioactive polypeptide or antibody conjugates described herein can be delivered intravenously, intraarterially or intraductally, or may be introduced locally at the intended site of action.

Molecules of the present invention can be used to identify and isolate receptors involved in growth and differentiation of zCTGF4 responsive cells. For example, proteins and peptides of the present invention can be immobilized on a column and membrane preparations run over the column (*Immobilized Affinity Ligand Techniques*, Hermanson et al., eds., Academic Press, San Diego, Calif., 1992, pp.195–202). Proteins and peptides can also be radiolabeled (*Methods in Enzymol.*, vol. 182, "Guide to Protein Purification", M. Deutscher, ed., Acad. Press, San Diego, 1990, 721–737) or photoaffinity labeled (Brunner et al., *Ann. Rev. Biochem.* 62:483–514, 1993 and Fedan et al., *Biochem. Pharmacol.* 33:1167–1180, 1984) and specific cell-surface proteins can be identified.

The molecules of the present invention will be useful for regulating the growth and/or differentiation of zCTGF4 responsive cells. The polypeptides, nucleic acid and/or antibodies of the present invention can be used in treatment of disorders associated with unregulated growth in zCTGF4-responsive tissues. In particular, the molecules of the present may used to produce antagonists to treat or prevent development of pathological conditions in tissues as testis, trachea, bone marrow, and kidney. Certain diseases such as bone marrow fibrosis, prevention of scar tissue formation, cutaneous lupus erythematosis, scleroderma, dermatositis, and end-stage kidney failure, may be amenable to such diagnosis, treatment or prevention.

Polynucleotides encoding zCTGF4 polypeptides are useful within gene therapy applications where it is desired to increase or inhibit zCTGF4 activity. If a mammal has a mutated or absent zCTGF4 gene, the zCTGF4 gene can be introduced into the cells of the mammal. In one embodiment, a gene encoding a zCTGF4 polypeptide is introduced in vivo in a viral vector. Such vectors include an attenuated or defective DNA virus, such as, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSV1) vector (Kaplitt et al., *Molec. Cell. Neurosci.* 2:320–30, 1991); an attenuated adenovirus vector, such as the vector described by Stratford-Perricaudet et al., *J. Clin. Invest.* 90:626–30, 1992; and a defective adeno-associated virus vector (Samulski et al., *J. Virol.* 61:3096–101, 1987; Samulski et al., *J. Virol.* 63:3822–28, 1989).

In another embodiment, the zCTGF4 gene can be introduced in a retroviral vector, e.g., as described in Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; International Patent Publication No. WO 95/07358, published Mar. 16, 1995 by Dougherty et al.; and Kuo et al., *Blood* 82:845–852, 1993. Alternatively, the vector can be introduced by lipofection in vivo using liposomes. Synthetic cationic lipids can be used to prepare liposomes for in vivo transfection of a gene encoding a marker (Felgner et al., *Proc. Natl. Acad. Sci. USA* 84:7413–17, 1987; Mackey et al., *Proc. Natl. Acad. Sci. USA* 85:8027–31, 1988). The use of lipofection to introduce exogenous genes into specific organs in vivo has certain practical advantages. Molecular targeting of liposomes to specific cells represents one area of benefit. More particularly, directing transfection to particular cells represents one area of benefit. For instance, directing transfection to particular cell types would be particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

It is possible to remove the target cells from the body; to introduce the vector as a naked DNA plasmid; and then to re-implant the transformed cells into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963–67, 1992; Wu et al., *J. Biol. Chem.* 263:14621–24, 1988.

Antisense methodology can be used to inhibit zCTGF4 gene transcription, such as to inhibit cell proliferation in vivo. Polynucleotides that are complementary to a segment of a zCTGF4-encoding polynucleotide (e.g., a polynucleotide as set forth in SEQ ID NO:1) are designed to bind to zCTGF4-encoding mRNA and to inhibit translation of such mRNA. Such antisense polynucleotides are used to inhibit expression of zCTGF4 polypeptide-encoding genes in cell culture or in a subject.

The present invention also provides reagents which will find use in diagnostic applications. For example, the zCTGF4 gene, a probe comprising zCTGF4 DNA or RNA or a subsequence thereof can be used to determine if the zCTGF4 gene is present on chromosome 6 or if a mutation has occurred. Detectable chromosomal aberrations at the zCTGF4 gene locus include, but are not limited to, aneuploidy, gene copy number changes, insertions, deletions, restriction site changes and rearrangements. Such aberrations can be detected using polynucleotides of the present invention by employing molecular genetic techniques, such as restriction fragment length polymorphism (RFLP) analysis, short tandem repeat (STR) analysis employing PCR techniques, and other genetic linkage analysis techniques known in the art (Sambrook et al., *ibid.;* Ausubel et. al., *ibid.;* Marian, *Chest* 108:255–65, 1995).

Mice engineered to express the zCTGF4 gene, referred to as "transgenic mice," and mice that exhibit a complete absence of zCTGF4 gene function, referred to as "knockout mice," may also be generated (Snouwaert et al., *Science* 257:1083, 1992; Lowell et al., *Nature* 366:740–42, 1993; Capecchi, M. R., Science 244: 1288–1292, 1989; Palmiter, R. D. et al. *Annu Rev Genet.* 20: 465–499, 1986). For example, transgenic mice that over-express zCTGF4, either ubiquitously or under a tissue-specific or tissue-restricted promoter can be used to ask whether over-expression causes a phenotype. For example, over-expression of a wild-type zCTGF4 polypeptide, polypeptide fragment or a mutant thereof may alter normal cellular processes, resulting in a phenotype that identifies a tissue in which zCTGF4 expression is functionally relevant and may indicate a therapeutic target for the zCTGF4, its agonists or antagonists. Moreover, such over-expression may result in a phenotype that shows similarity with human diseases. Similarly, knockout zCTGF4 mice can be used to determine where zCTGF4 is absolutely required in vivo. The phenotype of knockout mice is predictive of the in vivo effects of that a zCTGF4 antagonist, such as those described herein, may have. The human zCTGF4 cDNA can be used to isolate murine zCTGF4 mRNA, cDNA and genomic DNA, which are subsequently used to generate knockout mice. These mice may be employed to study the zCTGF4 gene and the protein encoded thereby in an in vivo system, and can be used as in vivo models for corresponding human diseases. Moreover, transgenic mice expression of zCTGF4 antisense polynucleotides or ribozymes directed zCTGF4, described herein, can be used analogously to transgenic mice described above.

For pharmaceutical use, the proteins of the present invention are formulated for parenteral, particularly intravenous or subcutaneous, delivery according to conventional methods. Intravenous administration will be by bolus injection or infusion over a typical period of one to several hours. In general, pharmaceutical formulations will include a zCTGF4 protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remington: *The Science and Practice of Pharmacy*, Gennaro, ed., Mack Publishing Co., Easton, Pa., 19th ed., 1995. Therapeutic doses will generally be in the range of 0.1 to 100 $\mu$g/kg of patient weight per day, preferably 0.5–20 $\mu$g/kg per day, with the exact dose determined by the clinician according to accepted standards, taking into account the nature and severity of the condition to be treated, patient traits, etc. Determination of dose is within the level of ordinary skill in the art. The proteins may be administered for acute treatment, over one week or less, often over a period of one to three days or may be used in chronic treatment, over several months or years.The invention is further illustrated by the following non-limiting examples.

The invention is further illustrated by the following non-limiting examples.

EXAMPLES

Example 1

Scanning of a translated DNA database using the CTGF family motifs as a query resulted in identification of an EST sequence found to have some homology to the connective tissue growth factor family.

Plasmid DNA was isolated from a clone corresponding to the EST, which had been designated zCTGF4, and was analyzed for polynucleotide sequence. Upon alignment of the zCTGF4 cDNA and CTGF family, it was revealed that the clone contained a truncated cDNA sequence with an intron at the 5' end of the sequence.

Based on the tissue distribution from Northern blot analysis (see Example 2), a cDNA library was constructed from human testis, and used to screen for a full length clone. The library was calculated to contain approximately $10^6$ clones. The master plate containing 80 pools (each pool representing 12 pools of $1.25 \times 10^4$ clones) was screened using PCR to determine whether zCTFG4 cDNA was present. Reactions were set up using: 1 μl of each pool, 20 pmoles each of oligonucleotide primers ZC14,882 and ZC14,883 (SEQ ID NOS: 6 and 7, respectively), and 1 U of ExTaq® DNA polymerase (TaKaRa Shuzo Co., Ltd., Shiga, JP) in a 25 μl volume. PCR was performed in a 96-well plate on a GenAmp PCR system 9700 (PE Applied Biosystems, Cheshire, UK). The reaction was run as follows: 94° C. for 1.5 minute, then for 30 cycles of 94° C., 15 seconds; 55° C. 20 seconds; 72° C. 30 seconds; and ended with a 7 minute incubation at 72° C. Pools designated A3, A6, D3, D6 and F7 were positive for the presence of zCTGF4 DNA, and selected for further analyses.

Positive pools were further analyzed with PCR to identify clones with longer 5' end sequence. The reaction mixture contained: 1 μl of each pool, 20 pmoles each of oligonucleotide primers ZC15,909 (corresponding to a vector sequence) and ZC14,885 (corresponding to a gene specific sequence) (SEQ ID NOS: 8 and 9, respectively), and 1 U of mixture ExTaq (TaKaRa) and Pfu® (Stratagene, La Jolla, Calif.) (2:1) DNA polymerase, in a 25 μl total volume. PCR was performed on a GenAmp PCR system 2400 (PE Biosystems) as follows: 94° C. for 1.5 minute, then for 25 cycles of 94° C., 15 seconds; 55° C. 20 seconds; 72° C. 30 seconds; 7 minute incubation at 72° C. A second nested anchor PCR was performed using 1 μl of 1/50 diluted first round PCR products as template, 20 pmoles each of oligonucleotide primers ZC15,911 (corresponding to vector sequence) and ZC14,884 (corresponding to gene specific sequence) (SEQ ID NOS: 10 and 11, respectively), and 1 U of mixture ExTaq (TaKaRa) and Pfu® (Stratagene) (2:1) DNA polymerase in a 25 μl total volume. The reaction was run as follows: 94° C. for 1.5 minute, then for 25 cycles of 94° C., 15 seconds; 50° C. 20 seconds; 72° C. 30 seconds; 7 minute incubation at 72° C. PCR products from A3, A6, D3 and D6 were gel purified with QIAquick Gel Extraction kit (Qiagen Inc. Chatsworth, Calif.), subcloned into a pCR2.1 vector of TA Cloning® kit (Invitrogen, Carlsbad, Calif.), which provides for direct ligation into expression vectors (Mead et al., *Bio/Technology* 9(7):657–663, 1991), and designated as CTGF4a3, CTGF4a6, CTGF4d3, CTGF4d6.

Sequence analysis of CTGF4a3, CTGF4a6, CTGF4d3, and CTGF4d6 revealed that the sequence of CTGF4a3 encoded a start Met with a putative signal peptide, a long open reading frame (ORF) at which the first reading frame was interrupted by a stop codon, and a short ORF thereafter at the second reading frame. The short ORF was identical to the 5' end coding region of zCTGF4, while the long ORF had a 45% sequence similarity to human CTGF. The sequence of CTGF4a6 was almost identical to CTGF4a3 except it was short 16 N-terminal amino acids in the secretory signal peptide. Both CTGF4d3 and CTGF4d6 had smaller inserts. All four clones encoded a long ORF interrupted by a stop codon at same place.

A PCR approach, as described previously, was used to find a correctly coded sequence in other tissues. A human bone marrow marathon cDNA was used based on the results of northern blot analysis (see Example 2). cDNA was made using Clontech Marathon™ cDNA kit (Clontech, Palo Alto, Calif.), according to the manufacturer's specifications. 5 μl of 1/100 diluted Marathon™ bone marrow cDNA, 20 pmoles each of oligonucleotide primers ZC15,910 and ZC14,885 (SEQ ID NOS: 12 and 9, respectively), and 1 U of ExTaq (TaKaRa) and Pfu® (Stratagene) (2:1) DNA polymerase were used in a 25 μl of reactions. The reactions were run as follows: 94° C. for 1.5 minute, then for 25 cycles of 94° C., 15 seconds; 54° C. 20 seconds; 72° C. 30 seconds; and ended with a 7 minute incubation at 72° C. 1 μl of 1/50 diluted first PCR product was used as template for nested PCR. 20 pmoles each of oligonucleotide primers ZC16,192 and ZC14,884 (SEQ ID NOS: 13 and 11, respectively), and 1 U of ExTaq (TaKaRa) and Pfu® (Stratagene) (2:1) DNA polymerase were used in a 25 μl of reactions. The reactions were run as follows: 94° C. for 1.5 minute, then for 25 cycles of 94° C., 15 seconds; 50° C. 20 seconds; 72° C. 30 seconds; and ended with a 7 minute incubation at 72° C. The PCR product was gel purified, subcloned into pCR2.1 vector (as described previously), and sequenced. The sequence analysis revealed that the 5' and 3' end of bone marrow clone overlapped with the testis clones, with a discrepancy in the region having the reading frame shift in the testis clone. The sequence of bone marrow clone had a correct ORF, and was included in the composite full length sequence of zCTGF4. The initially identified EST, which originated from a penis library, as well as clones identified from two testis libraries, had introns or reading frame shifts in the same region. Further analysis revealed that this region was least conserved area when compared to other members in the family, suggesting the reading frame shift may be a regulatory mechanism.

Example 2

Northern analyses were performed using Human Multiple Tissue Blots I, II and III from Clontech (Palo Alto, Calif.). A probe was generated from a gel purified PCR product made from ZC14,883 (SEQ ID NO: 7) and ZC14,882 (SEQ ID NO: 6) as primers and zCTGF4 as template, that had been radioactively labeled with REDIPRIME™ DNA labeling kit (Amersham, Arlington Heights, Ill.) according to the manufacturer's suggestion. The probe was purified using a NUC-TRAP push column (Stratagene). EXPRESSHYB™ (Clontech) solution was used for prehybridization and as a hybridizing solution for the Northern blots. Hybridization took place overnight at 65° C., and the blots were then washed in 2×SSC and 0.05% SDS at RT, followed by a wash in 0.1×SSC and 0.1% SDS at 50° C. One major transcript was observed at size of 1.4 kb. Signals were present in testis, bone marrow, trachea, kidney, liver, stomach, small intestine, ovary, placenta, prostate and spinal cord. The expression of zCTGF4 was also examined with Human RNA Master blot (Clontech) with a probe generated from a PCR product amplified with ZC16,192 (SEQ ID NO: 13) and ZC14,884 (SEQ ID NO: 11) as primers and zCTGF4 as template DNA. The conditions for probe labeling and hybridization were the same as described above. zCTGF4 was positive in two other tissues, mammary gland and fetal kidney, in addition to those described above.

Example 3 zCTGF4 was mapped to chromosome 6 using the commercially available "GeneBridge 4 Radiation Hybrid Panel" (Research Genetics, Inc., Huntsville, Ala.). The GeneBridge 4 Radiation Hybrid Panel contained DNAs from each of 93 radiation hybrid clones, plus two control DNAs (the HFL donor and the A23 recipient). A publicly available WWW server (http://www-genome.wi.mit.edu/cgi-bin/contig/rhmapper.pl) allowed mapping relative to the Whitehead Institute/MIT Center for Genome Research's radiation hybrid map of the human genome (the "WICGR" radiation hybrid map) which was constructed with the GeneBridge 4 Radiation Hybrid Panel.

For the mapping of zCTGF4 with the "GeneBridge 4 RH Panel", 20 µl reactions were set up in a 96-well microtiter plate (Stratagene, La Jolla, Calif.), and used in a "RoboCycler Gradient 96" thermal cycler (Stratagene). Each of the 95 PCR reactions consisted of 2 µl 10×KlenTaq PCR reaction buffer (CLONTECH Laboratories, Inc., Palo Alto, Calif.), 1.6 µl dNTPs mix (2.5 mM each, PERKIN-ELMER, Foster City, Calif.), 1 µl sense primer, ZC15,089 (SEQ ID NO: 14), 1 µl antisense primer, ZC15,092 (SEQ ID NO: 15), 2 µl "RediLoad" (Research Genetics, Inc., Huntsville, Ala.), 0.4 µl 50×Advantage KlenTaq Polymerase Mix (Clontech Laboratories, Inc.), 25 ng of DNA from an individual hybrid clone or control and ddH$_2$O for a total volume of 20 µl. The reactions were overlaid with an equal amount of mineral oil and sealed. The PCR cycler conditions were as follows: an initial 1 cycle 5 minute denaturation at 95° C., 35 cycles of a 1 minute denaturation at 95° C., 1 minute annealing at 56° C. and 1.5 minute extension at 72° C., followed by a final 1 cycle extension of 7 minutes at 72° C. The reactions were separated by electrophoresis on a 2% agarose gel (GIBCO-BRL Life Technologies, Gaithersburg, Md.).

The results showed that zCTGF4 maps 6.29 cR_3000 from the framework marker WI-4792 on the WICGR chromosome 6 radiation hybrid map. Proximal and distal framework markers were WI-4792 and CHLC.GATA31.100, respectively. The use of surrounding markers positions zCTGF4 in the 6q22.1 region on the integrated LDB chromosome 6 map (The Genetic Location Database, University of Southhampton, WWW server: http://cedar.genetics.soton.ac.uk/public_html/).

Example 4

Several expression constructs were made for eukaryotic expression of the zCTGF4 cDNA. A mammalian expression vector was constructed with the dihyrofolate reductase gene under control of the SV40 early promoter, SV40 polyadenylation site, a cloning site to insert the gene of interest under control of the MT-1 promoter and the hGH polyadenylation site. The expression vector was designated pZP9 and is deposited at the American Type Culture Collection, 12301 Parklawn Drive, Rockville, Md. To facilitate purification, pZP9 vector was modified by addition of the tPA leader sequence (U.S. Pat. No. 5,641,655, incorporated herein by reference) and a GluGlu tag (SEQ ID NO: 16) between the MT-1 promoter and hGH terminator. The tPA leader replaces the native secretory signal sequence for DNAs encoding for polypeptides of interest that are inserted into this vector, and expression results in an N-terminally tagged protein. The N-terminally tagged vector was designated pZP9NEE. Another vector was similarly constructed with a C-terminal GluGlu tag (SEQ ID NO: 16) inserted just 5' to the hGH terminator and utilizes the native (or other fused) secretory signal sequence for secretion of the encoded polypeptide of interest, and expression resulted in a C-terminally tagged protein. The C-terminal GluGlu tagged vector was designated pZP9CEE.

A 5' DNA fragment containing the zCTGF4 coding region (nucleotide 86 to nucleotide 613 of SEQ ID NO: 1) was generated by PCR using oligonucleotide primers ZC16,422 (SEQ ID NO: 17) and ZC16,424 (SEQ ID NO: 18) and CTGF4A3 as the template, and a 3' DNA fragment including nucleotide 590 to nucleotide 1078 of SEQ ID NO: 1 and oligonucleotides ZC16,421 (SEQ ID NO: 19) and ZC16,425 (SEQ ID NO: 20) as primers and zCTGF4 as template. The PCR reactions were run as follows: 1 cycle at 94° C. for 1.5 minutes; 3 cycles of 94° C. for 15 seconds; 50° C. for 30; 72° C. for 30 seconds; 12 cycles of 94° C. for 15 seconds; 50° C. for 20 seconds; 72° C. for 30 seconds and 1 cycle at 72° C. for 2 minutes. The PCR products were gel purified and mixed together as the template for the following PCR reaction: 1 cycle at 94° C. for 1.5 minutes; 3 cycles of 94° C. for 15 seconds; 54° C. for 20; 68° C. for 45 seconds; 20 cycles of 94° C. for 15 seconds; 68° C. for 45 seconds; and 1 cycle at 72° C. for 2 minutes. This PCR product, which contained the entire polynucleotide sequence encoding for the mature zCTGF4 polypeptide, was gel purified and restriction digested with BamH I and Xho I for use with the N-terminally tagged vector, pZP9NEE, described above. The zCTGF4 DNA sequence was ligated into the vector pZP9NEE and E. coli transformants selected, and designated pZP9NEE/zCTGF4.

Plasmid DNA was isolated and the region of the plasmid containing polynucleotides encoding for the tPA leader followed by the DNA encoding the GluGlu tag (SEQ ID NO: 16) and mature CTGF4 polypeptide were excised using a 5' EcoR I and a 3' XbaI site. The insert was sequence analyzed for verification.

A similar cloning method was used to generate a C-terminally tagged expression construct. This construct, designated pZP9CEE/zCTGF4 comprises the pZP9CEE vector with DNAs encoding for the native zCTGF4 secretory signal sequence, the mature zCTGF4 polypeptide (shown in SEQ ID NO: 1) and a C-terminal GluGlu tag (SEQ ID NO: 16).

The fragment from pZP9NEE/zCTGF4 containing DNA encoding for the the tPA secretory signal peptide, the GluGlu tag and the mature zCVTGF4 were ligated into a baculovirus vector designated pZBV4L. pZBV4L is a baculovirus expression vector derived from the FASTBAC vector of the Bac-to-Bac™ system (GIBCO-BRL, Gaithersburg, Md.) and described in Luckow et al., J. Virol. 67:4566–4579, 1993. The pFASTBAC vector was modified by removing the polyhedrin promoter and substituting the baculovirus basic protein promoter (Hill-Perkins et al., J. Gen. Virol. 71:971–976, 1990; Bonning et al., J. Gen. Virol. 75:1551–1556, 1994; and Chazenbalk et al., J. Biol. Chem. 270:1543–1549, 1995).

One microliter of zCTGF4NEE/pZBV4L expression construct is used to transform 20 µl DH10Bac (GIBCO-BRL, Gaithersburg, Md.) in 980 µl SOC (2% Bacto Tryptone, 0.5% Bacto Yeast Extract, 10 ml 1M NaCl, 1.5 mM KCl, 10 mM MgCl$_2$, 10 mM MgSO$_4$ and 20 mM glucose), according to the manufacturer's specifications. The cells are incubated 48 hours at 37° C. and 2 colonies in which virus had incorporated the plasmid (referred to as a "bacmid") were identified (white in color), and are isolated. Bacmid DNA is isolated and used to transfect Spodoptera frugiperda (Sf9) cells using transfection liposomes from Cellfectin (GIBCO-BRL). The cells are cultured at 27° C. in shake flasks using 50–100 ml of Sf900II serum free medium (GIBCO-BRL). After 3–4 days medium conditioned by the virus is harvested and used to infect Sf9 cells in mid-log growth at approximately 1E6 cells/ml.

The cells are scaled up by adding cell cultures to volumes of 15 liter when cells have achieved a density between 1-2E6 cell/ml and then infected with an MOI of 1-3. After 2 days at 27° C., the medium containing the protein and virus is harvested.

Example 5

A. Affinity Tagged zCTGF4 Protein zCTGF4 expressed with an N-terminal or C-terminal GluGlu (EE) tag is purified as follows: A mixture of protease inhibitors is added to a 2000 ml sample of conditioned media from baculovirus-infected Sf9 cells to final concentrations of 2.5 mM ethylenediaminetetraacetic acid (EDTA, Sigma Chemical Co. St. Louis, Mo.), 0.001 mM leupeptin (Boehringer-Mannheim, Indianapolis, Ind.), and 0.001 mM pepstatin (Boehringer-Mannheim) and 0.4 mM Pefabloc (Boehringer-Mannheim). The sample is centrifuged at 10,000 rpm for 30 min at 4° C. in a Beckman JLA-10.5 rotor (Beckman Instruments, Palo Alto, Calif.) in a Beckman Avanti J25I centrifuge (Beckman Instruments) to remove cell debris. To the supernatant fraction is added a 50.0 ml sample of anti-EE Sepharose, prepared as described below, and the mixture is gently agitated on a Wheaton (Millville, N.J.) roller culture apparatus for 18.0 h at 4° C.

The mixture is poured into a 5.0×20.0 cm Econo-Column (Bio-Rad, Laboratories, Hercules, Calif.) and the gel is washed with 30 column volumes of phosphate buffered saline (PBS). The unretained flow-through fraction is discarded. When the absorbance of the effluent at 280 nM is less than 0.05, flow through the column is reduced to zero and the anti-EE Sepharose gel is washed with 2.0 column volumes of PBS containing 0.2 mg/ml of EE peptide (AnaSpec, San Jose, Calif.). The peptide used has the sequence GluTyrMetGlu (SEQ ID NO: 16). After 1.0 h at 4° C., flow is resumed and the eluted protein is collected. This fraction is the peptide elution. The anti-EE Sepharose gel is washed with 2.0 column volumes of 0.1M glycine, pH 2.5, and the glycine wash is collected separately. The pH of the glycine-eluted fraction is adjusted to 7.0 by the addition of a small volume of 10×PBS and stored at 4° C.

The peptide elution is concentrated to 5.0 ml using a 15,000 molecular weight cutoff membrane concentrator (Millipore, Bedford, Mass.), according to the manufacturer's instructions. The concentrated peptide elution is separated from free peptide by chromatography on a 1.5×50 cm Sephadex G-50 (Pharmacia, Piscataway, N.J.) column equilibrated in PBS at a flow rate of 1.0 ml/min using a BioCad Sprint HPLC (PerSeptive BioSystems, Framingham, Mass.). Two-ml fractions are collected and the absorbance at 280 nM is monitored. The first peak of material absorbing at 280 nM and eluting near the void volume of the column is collected. This fraction is pure N-terminally tagged zCTGF4 or C-terminally tagged zCTGF4. The pure material is concentrated as described above, analyzed by SDS-PAGE and Western blotting with antiEE antibodies, aliquoted, and stored at −80° C.

Preparation of anti-EE Sepharose is done as follows: A 100 ml bed volume of protein G-Sepharose (Pharmacia, Piscataway, N.J.) is washed 3 times with 100 ml of PBS containing 0.02% sodium azide using a 500 ml Nalgene 0.45 micron filter unit. The gel is washed with 6.0 volumes of 200 mM triethanolamine, pH 8.2 (TEA, Sigma, St. Louis, Mo.), and an equal volume of EE antibody solution containing 900 mg of antibody is added. After an overnight incubation at 4° C., unbound antibody is removed by washing the resin with 5 volumes of 200 mM TEA as described above. The resin is resuspended in 2 volumes of TEA, transferred to a suitable container, and dimethylpimilimidate-2HCl (Pierce, Rockford, Ill.), dissolved in TEA, is added to a final concentration of 36 mg/ml of gel. The gel is rocked at room temperature for 45 min and the liquid is removed using the filter unit as described above. Nonspecific sites on the gel are then blocked by incubating for 10 min. at room temperature with 5 volumes of 20 mM ethanolamine in 200 mM TEA. The gel is then washed with 5 volumes of PBS containing 0.02% sodium azide and stored in this solution at 40° C.

B. Untagged zCTGF4 Protein

Protease inhibitors are added to the conditioned media of baculovirous-infected Sf9 cells and the media will be centrifuged as described above for the EE-tagged proteins. The supernatant fraction is applied to a 50.0 ml column of POROS HE1 (PerSeptive BioSystems, Framingham, Miss.) pre-equilibrated in 20 mM Tris-HCl, 50 mM NaCl, pH 7.4 at a flow rate of 2.0 ml/min with in-line dilution (three-fold final dilution) with water as diluent using a BioBad Sprint HPLC (PerSeptive BioSystems, Framingham, Miss.). Heparin-bound proteins are eluted with a 0.1–1.0 M gradient of NaCl. Protein-containing fractions are identified by absorbance at 280 nM and by SDS-PAGE. Fractions containing zCTGF4 are identified by a band on SDS-PAGE gels of the appropriate molecular weight for glycosylated zCTGF4 of approximately 40 kDa The heparin-bound zCTGF4 pool is concentrated, applied to a Sephadex-G50 or a -G100 column, and eluted as described above. Purified zCTGF4 is characterized by SDS-PAGE, amino acid analysis, and N-terminal sequencing.

Example 6

A. Adenoviral Expression of zCTGF4

The protein coding region of zCTGF4 was amplified by PCR using primers that added FseI and AscI restriction sties at the 5' and 3' termini respectively. PCR primers ZC17948 (SEQ. ID. NO: 29) and ZC17949 (SEQ ID NO: 30) were used with a template containing the full-length zCTGF4 cDNA in a PCR reaction as follows: one cycle at 95° C. for 5 minutes; followed by 15 cycles at 95° C. for 1 min., 58° C. for 1 min., and 72° C. for 1.5 min.; followed by 72° C. for 7 min.; followed by a 4° C. soak. The PCR reaction product was loaded onto a 1.2 % (low melt) SeaPlaque GTG (FMC, Rockland, Me.) gel in TAE buffer. The zCTGF4 PCR product was excised from the gel and purified using the QIAquick™ PCR Purification Kit gel cleanup kit as per kit instructions (Qiagen). The PCR product was then digested with FseI-AscI, phenol/chloroform extracted, EtOH precipitated, and rehydrated in 20 ml TE (Tris/EDTA pH 8). The 1065 bp zCTGF4 fragment was then ligated into the FseI-AscI sites of the transgenic vector pTG12-8 (See, description herein) and transformed into DH10B competent cells by electroporation. Clones containing zCTGF4 were identified by plasmid DNA miniprep followed by digestion with FseI-AscI. A positive clone was confirmed by direct sequencing.

B. Preparation of DNA Construct for Generation of Adenovirus

The 1065 bp zCTGF4 cDNA was released from a TG12-8 vector using FseI and AscI enzymes. The cDNA was isolated on a 1% low melt SeaPlaque GTGTM (FMC, Rockland, Me.) gel, and was then excised from the gel. The gel slice was melted at 70° C., extracted twice with an equal volume of Tris buffered phenol, and EtOH precipitated. The DNA was resuspended in 10 $\mu$l $H_2O$.

The zCTGF4 cDNA was cloned into the FseI-AscI sites of a modified pAdTrack CMV (He et al., PNAS 95:2509–2514, 1998). This construct contains the GFP marker gene. The CMV promoter driving GFP expression was replace with the SV40 promoter and the SV40 polyadenylation signal was replaced with the human growth hormone polyadenylation signal. In addition, the native polylinker was replaced with FseI, EcoRV, and AscI sites. This modified form of pAdTrach CMV was named pZyTrack. Ligation was performed using the Fast-Link™ DNA ligation and screening kit (Epicentre Technologies, Madison, Wis.). In order to linearize the plasmid, approximately 5 μg of the pZyTrack zctgf4 plasmid was digested with PmeI. Approximately 1 μg of the linearized plasmid was cotransformed with 200 ng of supercoiled pAdEasy (He et al., supra.) into BJ5183 cells. The co-transformation was done using a Bio-Rad Gene Pulser at 2.5 kV, 200 ohms and 25mFa. The entire co-transformation was plated on 4 LB plates containing 25 μg/ml kanamycin. The smallest colonies were picked and expanded in LB/kanamycin and recombinant adenovirus DNA identified by standard DNA miniprep procedures. Digestion of the recombinant adenovirus DNA with FseI-AscI confirmed the presence of zCTGF4. The recombinant adenovirus miniprep DNA was transformed into DH10B competent cells and DNA prepared using a Qiagen maxi prep kit as per kit instructions.

C. Transfection of 293A Cells with Recombinant DNA

Approximately 5 μg of recombinant adenoviral DNA was digested with PacI enzyme (New England Biolabs) for 3 hours at 37° C. in a reaction volume of 100 μl containing 20–30 U of PacI. The digested DNA was extracted twice with an equal volume of phenol/chloroform and precipitated with ethanol. The DNA pellet was resuspended in 10 μl distilled water. A T25 flask of QBI-293A cells (Quantum Biotechnologies, Inc. Montreal, Qc. Canada), inoculated the day before and grown to 60–70% confluence, were transfected with the PacI digested DNA. The PacI-digested DNA was diluted up to a total volume of 50 μl with sterile HBS (150 mM NaCl, 20 mM HEPES). In a separate tube, 20 μl DOTAP (Boehringer Mannheim, 1 mg/ml) was diluted to a total volume of 100 μl with HBS. The DNA was added to the DOTAP, mixed gently by pipeting up and down, and left at room temperature for 15 minutes. The media was removed from the 293A cells and washed with 5 ml serum-free MEM-alpha (Gibco BRL) containing 1 mM Sodium Pyruvate (GibcoBRL), 0.1 mM MEM non-essential amino acids (GibcoBRL) and 25 mM HEPES buffer (GibcoBRL). 5 ml of serum-free MEM was added to the 293A cells and held at 37° C. The DNA/lipid mixture was added drop-wise to the T25 flask of 293A cells, mixed gently and incubated at 37° C. for 4 hours. After 4 h the media containing the DNA/lipid mixture was aspirated off and replaced with 5 ml complete MEM containing 5% fetal bovine serum. The transfected cells were monitored for Green Fluorescent Protein (GFP) expression and formation of foci, i.e., viral plaques.

Seven days after transfection of 293A cells with the recombinant adenoviral DNA, the cells expressed the GFP protein and started to form foci. These foci are viral "plaques" and the crude viral lysate was collected by using a cell scraper to collect all of the 293A cells. The lysate was transferred to a 50 ml conical tube. To release most of the virus particles from the cells, three freeze/thaw cycles were done in a dry ice/ethanol bath and a 37° waterbath.

D. Amplification of Recombinant Adenovirus (rAdV)

The crude lysate was amplified (Primary (1°) amplification) to obtain a working "stock" of zCTGF4 rAdV lysate. Ten 10 cm plates of nearly confluent (80–90%) 293A cells were set up 20 hours previously, 200 ml of crude rAdV lysate added to each 10 cm plate and monitored for 48 to 72 hours looking for CPE under the white light microscope and expression of GFP under the fluorescent microscope. When all of the 293A cells showed CPE (Cytopathic Effect) this 1° stock lysate was collected and freeze/thaw cycles performed as described under Crude rAdV Lysate.

Secondary (2°) Amplification of zCTGF4 rAdV was obtained as follows: Twenty 15 cm tissue culture dishes of 293A cells were prepared so that the cells were 80–90% confluent. All but 20 mls of 5% MEM media was removed and each dish was inoculated with 300–500 ml 10 amplified rAdv lysate. After 48 hours the 293A cells were lysed from virus production and this lysate was collected into 250 ml polypropylene centrifuge bottles and the rAdV purified.

E. AdV/cDNA Purification

NP-40 detergent was added to a final concentration of 0.5% to the bottles of crude lysate in order to lyse all cells. Bottles were placed on a rotating platform for 10 min. agitating as fast as possible without the bottles falling over. The debris was pelleted by centrifugation at 20,000×G for 15 minutes. The supernatant was transferred to 250 ml polycarbonate centrifuge bottles and 0.5 volumes of 20% PEG8000/2.5M NaCl solution added. The bottles were shaken overnight on ice. The bottles were centrifuged at 20,000×G for 15 minutes and supernatant discarded into a bleach solution. The white precipitate in two vertical lines along the wall of the bottle on either side of the spin mark is the precipitated virus/PEG. Using a sterile cell scraper, the precipitate from 2 bottles was resuspended in 2.5 ml PBS. The virus solution was placed in 2 ml microcentrifuge tubes and centrifuged at 14,000×G in the microfuge for 10 minutes to remove any additional cell debris. The supernatant from the 2 ml microcentrifuge tubes was transferred into a 15 ml polypropylene snapcap tube and adjusted to a density of 1.34 g/ml with cesium chloride (CsCl). The volume of the virus solution was estimated and 0.55 g/ml of CsCl added. The CsCl was dissolved and 1 ml of this solution weighed 1.34 g. The solution was transferred polycarbonate thick-walled centrifuge tubes 3.2 ml (Beckman) and spin at 80,000 rpm (348,000×G) for 3–4 hours at 25° C. in a Beckman Optima TLX microultracentrifuge with the TLA-100.4 rotor. The virus formed a white band. Using wide-bore pipette tips, the virus band was collected.

The virus from the gradient has a large amount of CsCl which must be removed before it can be used on cells. Pharmacia PD-10 columns prepacked with Sephadex G-25M (Pharmacia) were used to desalt the virus preparation. The column was equilibrated with 20 ml of PBS. The virus was loaded and allowed to run into the column. 5 ml of PBS was added to the column and fractions of 8–10 drops collected. The optical densities of 1:50 dilutions of each fraction was determined at 260 nm on a spectrophotometer. A clear absorbance peak was present between fractions 7–12. These fractions were pooled and the optical density (OD) of a 1:25 dilution determined. A formula is used to convert OD into virus concentration: (OD at 260 nm)(25) $(1.1 \times 10)$ =virions/ml. The OD of a 1:25 dilution of the zctgf4 rAdV was 0.221, giving a virus concentration of $6 \times 10^{12}$ virions/ml.

To store the virus, glycerol was added to the purified virus to a final concentration of 15%, mixed gently but effectively, and stored in aliquots at −80° C.

F. Tissue Culture Infectious Dose at 50% CPE (TCID 50) Viral Titration Assay

A protocol developed by Quantum Biotechnologies, Inc. (Montreal, Qc. Canada) was followed to measure recombinant virus infectivity. Briefly, two 96-well tissue culture plates were seeded with $1 \times 10^4$ 293A cells per well in MEM containing 2% fetal bovine serum for each recombinant virus to be assayed. After 24 hours 10-fold dilutions of each virus from $1 \times 10^{-2}$ to $1 \times 10^{-14}$ were made in MEM containing 2% fetal bovine serum. 100 μl of each dilution was placed in each of 20 wells. After 5 days at 37° C., wells were read either positive or negative for Cytopathic Effect (CPE) and a value for "Plaque Forming Units/ml" (PFU) is calculated.

$TCID_{50}$ formulation used was as per Quantum Biotechnologies, Inc., above. The titer (T) is determined from a plate where virus used is diluted from $10^{-2}$ to $10^{-14}$, and read 5 days after the infection. At each dilution a ratio (R) of positive wells for CPE per the total number of wells is determined.

To Calculate titer of the undiluted virus sample: the factor, "F"=1+d(S−0.5); where "S" is the sum of the ratios (R); and "d" is Log10 of the dilution series, for example, "d" is equal to 1 for a ten-fold dilution series. The titer of the undiluted sample is $T=10^{(1+F)}=TCID_{50}$/ml. To convert $TCID_{50}$/ml to pfu/ml, 0.7 is subtracted from the exponent in the calculation for titer (T). The zCTGF4 adenovirus had a titer of $7.1\times10^{10}$ pfu/ml.

Example 7

Transgenic Expression

Transgenic animals expressing zCTGF4 genes were made using adult, (B6D2f1, 2–8 months, (Taconic Farms)), pre-pubescent fertile females (donors) (B6C3f1, 4–5 weeks, (Taconic Farms)) and adult fertile females (B6D2f1, 2–4 months, (Taconic Farms)) as parents.

The donors were injected with approximately 8 IU/mouse of Pregnant Mare's Serum gonadotrophin (Sigma, St. Louis, Mo.) I.P., and 46–47 hours later, 8 IU/mouse of human Chorionic Gonadotropin (hCG (Sigma)) were administered I.P. to induce superovulation.

Fertilized eggs were collected and stored in a 37° C./5% $CO_2$ incubator until microinjection.

10–20 micrograms of plasmid DNA containing a cDNA of the zCTGF4 gene was linearized, gel-purified, and resuspended in 10 mM Tris pH 7.4, 0.25 mM EDTA pH 8.0, at a final concentration of 5–10 nanograms per microliter for microinjection.

Plasmid DNA was microinjected into harvested eggs and were penetrated with an injection needle, into one or both of the haploid pronuclei.

The following day 2-cell embryos were transferred into pseudopregnant recipients. The recipients were returned to cages in pairs, and allowed 19–21 days gestation. After birth, 19–21 days postpartum was allowed before weaning. The 25 weanlings were sexed and placed into separate sex cages, and a 0.5 cm biopsy (used for genotyping) was snipped off the tail with clean scissors.

Genomic DNA was prepared from the tail snips using a Qiagen Dneasy kit following the manufacturer's instructions. Genomic DNA was analyzed by PCR using primers designed to the human growth hormone (hGH) 3' UTR portion of the transgenic vector. A region unique to the human sequence was identified from an alignment of the human and mouse growth hormone 3' UTR DNA sequences, ensuring that the PCR reaction does not amplify the mouse sequence. Primers zc17251 (SEQ ID NO: 31) and zc17252 (SEQ ID NO: 32) amplify a 368 base pair fragment of hGH. In addition, primers zc17156 (SEQ ID NO: 33) and zc17157 (SEQ ID NO: 34), which hybridize to vector sequences and amplify the cDNA insert, were often used along with the hGH primers. In these experiments, DNA from animals positive for the transgene generated two bands, a 368 base pair band corresponding to the hGH 3' UTR fragment and a band of variable size corresponding to the cDNA insert.

Once 9 animals were confirmed to be transgenic (TG), they were back with C57B1/6 wild-type mates. As pups were born and weaned, the sexes were separated, and their tails snipped for genotyping.

To check for expression of a transgene in a live animal, a small partial hepatic biopsy was collected. The collected liver biopsy was transferred to a 14 ml polypropylene round bottom tube and snap frozen in liquid nitrogen and then stored on dry ice.

Analysis of the mRNA expression level of each transgene was done using an RNA solution hybridization assay. In addition, transgenic mice were observed to be smaller than wild-type mice from the same litter. Thymus and spleen weights were observed to be lower when normalized by brain-to-organ weights. Histological examination revealed that most of the transgenic mice had some pancreatic atrophy and some cardiomyopathy.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. An isolated polynucleotide acid molecule that encodes a connective tissue growth factor homolog polypeptide, wherein the polynucleotide molecule is selected from the group consisting of:

(a) a molecule having the nucleotide sequence of SEQ ID NO:1 from nucleotide 17 or 86 to nucleotide 1078; and
(b) a molecule having the nucleotide sequence of SEQ ID NO:3 from nucleotide 1 or 70 to nucleotide 1062.

* * * * *